US006177459B1

(12) United States Patent
Gayer et al.

(10) Patent No.: US 6,177,459 B1
(45) Date of Patent: *Jan. 23, 2001

(54) SUBSTITUTED HETEROCYCLIC COMPOUNDS AND THEIR USE AS FUNGICIDES

(75) Inventors: Herbert Gayer, Monheim; Bernd-Wieland Krüger, Bergisch Gladbach; Dietmar Kuhnt, Burscheid; Ulrich Heinemann, Leichlingen; Peter Gerdes, Aachen; Ralf Tiemann; Gerd Hanssler, both of Leverkusen; Klaus Stenzel, Düsseldorf; Stefan Dutzmann, Hilden, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/875,818

(22) PCT Filed: Aug. 22, 1996

(86) PCT No.: PCT/EP96/00383

§ 371 Date: Aug. 4, 1997

§ 102(e) Date: Aug. 4, 1997

(87) PCT Pub. No.: WO96/25398

PCT Pub. Date: Aug. 22, 1996

(30) Foreign Application Priority Data

Feb. 13, 1995 (DE) ............................................... 195 04 624
Sep. 4, 1995 (DE) ............................................... 195 32 345

(51) Int. Cl.⁷ ......................... A01N 43/08; C07D 307/42
(52) U.S. Cl. ........................................... 514/471; 549/491
(58) Field of Search ............................. 549/491; 514/471

(56) References Cited

FOREIGN PATENT DOCUMENTS

| WO A 94 10159 | 5/1994 | (WO) . |
| WO A 94 22844 | 10/1994 | (WO) . |
| WO A 95 26956 | 10/1995 | (WO) . |

OTHER PUBLICATIONS

Takase et al, "Preparation of oxime—etc. " of WO 95 26,956 Oct. 12, 1995, CA 124 :146156f (1996).*

Chemical Abstracts, vol. 124, no. 11, 11 March 1996, Columbus, Ohio, US; abstract no. 146156f. A. Takase et al.:Preparation of oxide–containing heterocyclic compounds as ... page 1258; column 2; XP002001849 see abstract.

Journal of the Chemical Society, 1953, Letchworth GB, pages 2274–2778. XP0021845 Badger et al.:"Polynuclear Heterocyclic Systems. Part VII. Sayntheses using the Elbs Reaction." siehe Seite 2774, die Verbindung mit der Formel (I).

Bulletin de la Societe Chimique de France, vol. 6, 1939, Paris FR, pages 1339–1347, XP002001846 N. Maxim et al.: "L'action des composes organomagnesiens mixtes sur les amides N–disubstituees de l'acide alpha–furancarbonique;" siehe Seite 1342, die Verbindung mit der Formel (V).

Chemische Bfrichte,vol. 41, 1908, Weinheim de, pages 2145–2156, XP002001847 J.V. Braun: "Die Einwirkung von Formaldehyd auf sekundare aromatische Amine." siehe Seite 2151, leter Absatz–Seite 2152, erster Absatz.

Journal of the American Chemical Society, vol. 73 No. 2. 15 Feb. 1951, DC US, pp. 772–774, XP002001848 M.G. Seeley et al.: "The Structure of the Isomeric Quinoline Dicyanides" siehe Seite 773, 2 Spalte, letter Absatz–Seite 774, 1. Spalte, erster Absatz.

* cited by examiner

*Primary Examiner*—Patricia L. Morris
(74) *Attorney, Agent, or Firm*—Norris, McLaughlin & Marcus, P.A.

(57) ABSTRACT

The invention relates to novel substituted heterocyclic compounds, to a plurality of processes for their preparation and to their use as fungicides, and to novel intermediates, to a plurality of processes for their preparation and to their use as fungicides.

8 Claims, No Drawings

SUBSTITUTED HETEROCYCLIC COMPOUNDS AND THEIR USE AS FUNGICIDES

This application is a 371 of PCT/EP96/00383 filed Jan. 31, 1996.

The invention relates to novel substituted heterocyclic compounds, to a plurality of processes for their preparation and to their use as fungicides, and to novel intermediates, to a plurality of processes for their preparation and to their use as fungicides.

Certain substituted heterocyclic compounds are known to have fungicidal properties (cf. EP-A 633252 and WO-A 9422844). However, the activity of these compounds, in particular at low application rates, is not entirely satisfactory in all areas of application.

This invention, accordingly, provides the novel substituted heterocyclic compounds of the general formula (I)

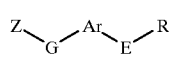
(I)

in which
Ar represents optionally substituted arylene or heteroarylene,

E represents a 1-alkene-1,1-diyl grouping which contains a radical $R^1$ in position 2, or represents a 2-aza-1-alkene-1,1-diyl grouping which contains a radical $R^2$ in position 2, or represents an optionally substituted imino grouping ("azamethylene", N-$R^3$), or represents a 3-aza-1-propene-2,3-diyl grouping which contains a radical $R^1$ in position 1 and a radical $R^3$ in position 3, or represents a 3-oza-1-propene-2,3-diyl grouping which contains a radical $R^1$ in position 1, or represents a 3-thia-1-propene-2,3-diyl grouping which contains a radical $R^1$ in position 1, or represents a 1-aza-1-propene-2,3-diyl grouping which contains a radical $R^2$ in position 1 and a radical $R^3$ in position 3, or represents a 1-aza-1-propene-2,3-diyl grouping which contains a radical R' in position 1 and a radical $R^3$ in position 3, or represents a 1,3-diaza-1-propene-2,3-diyl grouping which contains a radical $R^2$ in position 1 and a radical $R^3$ in position 3, or represents a 1-aza-3-oxa-1-propene-2,3-diyl grouping which contains a radical $R^2$ in position 1, or represents a 1-aza-3-thia-1-propene-2,3-diyl grouping which contains a radical $R^2$ in position 1, where $R^1$ represents hydrogen, halogen, cyano or represents respectively optionally substituted alkyl, alkoxy, alkylthio, alkylamino or dialkylamino, $R^2$ represents hydrogen, amino, hydroxyl, cyano or represents respectively optionally substituted alkyl, alkoxy, alkylamino or dialkylamino, and $R^3$ represents hydrogen, cyano, hydroxyl or represents respectively optionally substituted alkyl, alkoxy, alkoxyalkyl, alkenyl, alkinyl, cycloalkyl or cycloalkylalkyl, G represents a single bond, represents oxygen or sulphur or represents respectively optionally halogen-, hydroxyl-, alkyl-, halogenoalkyl- or cycloalkyl-substituted alkanediyl, alkenediyl, alkinediyl or one of the groupings below —Q—CQ—, —CQ—Q—, —$CH_2$—Q—; —Q—$CH_2$-, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^4$)=N—O—, —C($R^4$)=N—O—$CH_2$—, —N($R^5$)—, —CQ—N($R^5$)—, —N($R^5$)—CQ—, —Q—CQ—N($R^5$)—, —N=C($R^4$)—Q—$CH_2$—, —$CH_2$—O—N=C($R^4$)—, —N($R^5$)—CQ-Q-, —CQ-N($R^5$)—CQ—Q—, —N($R^5$)—CQ—Q—$CH_2$—, —Q—C($R^4$)=N—O—$CH_2$—, —N($R^5$)—C($R^4$)=N—O—$CH_2$—, —O—$CH_2$—C($R^4$)=N—O—$CH_2$—, —N=N—C($R^4$)=N—O—$CH_2$—, —T—$Ar^1$— or —T—$Ar^1$—Q—, where $Ar^1$ represents optionally substituted arylene, heteroarylene, cycloalkylene or heterocycloalkylene (i.e. an aliphatic ring which is attached twice and where one or more carbon atoms are replaced by hetero atoms, i.e. atoms that differ from carbon), n represents the numbers 0, 1 or 2, Q represents oxygen or sulphur, $R^4$ represents hydrogen, cyano or respectively optionally substituted alkyl, alkoxy, alkylthio, alkylamino, dialkylamino or cycloalkyl, and $R^5$ represents hydrogen, hydroxyl, cyano or respectively optionally substituted alkyl, alkoxy or cycloalkyl and T represents a single bond, represents oxygen, sulphur, —$CH_2$—O—, —$CH_2$—S— or represents optionally substituted alkanediyl and R represents pyrrolyl, imidazolyl, pyrazolyl, 1,2,3-triazolyl, 1,2,4-triazolyl or tetrazolyl, each of which is attached via a carbon atom and each of which is optionally alkyl-substituted at a nitrogen atom, represents 1,2,5-oxadiazolyl, furyl, thienyl, 1,2-thiazolyl, 1,3-thiazolyl, 4-oxo-1,3-thiazol-2-yl, 1,2,3-thiadiazolyl, 1,2,4-thiadiazolyl, 1,2,5-thiadiazolyl, 1,3,4-thiadiazolyl, pyridyl, pyrimidyl, pyrazyl, pyridazyl, 1,2,3-triazyl, 1,2,4-triazyl, 1,3,5-triazyl, partially or fully hydrogenated thiazolyl or thiazinyl, each of which is attached via a carbon atom and each of which is optionally substituted, represents respectively optionally substituted saturated heterocyclyl having at least one oxygen and/or at least one sulphur atom, or represents optionally substituted 1,3-diazacycloalk-1-en-2-yl, Z represents respectively optionally substituted alkyl, alkenyl, alkinyl, cycloalkyl, aryl or heterocyclyl.

Aryl represents aromatic mono- or polycyclic hydrocarbon rings, such as, for example, phenyl, naphthyl, anthranyl, phenanthryl, preferably phenyl or naphthyl, in particular phenyl.

Unless otherwise defined, heterocyclyl represents saturated or unsaturated, and aromatic, compounds in the form of a ring in which at least one ring member is a hetero atom, i.e. an atom different from carbon. If the ring contains more than one hetero atom, these may be identical or different. Preferred hetero atoms are oxygen, nitrogen and sulphur. Optionally, the compounds in the form of a ring may form a polycyclic ring system together with other carbocyclic or heterocyclic fused or bridged rings. Preference is given to mono- or bicyclic ring systems, in particular to mono- or bicyclic aromatic ring systems.

Furthermore, it has been found that the novel substituted heterocyclic compounds of the general formula (I) are obtained when a) ketones of the general formula (II)

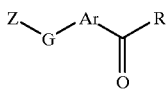
(II)

in which

Ar, G, R and Z are each as defined above are reacted with an amine of the formula (III)

R$^2$—NH2 (III)

in which

R$^2$ is as defined above, or an acid addition complex thereof, if appropriate in the presence of a diluent and if appropriate in the presence of a reaction auxiliary, or b) nitriles of the general formula (IV)

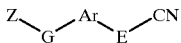
(IV)

in which

Ar, E, G and Z are each as defined above are reacted with a bifunctional alkylene compound of the general formula (V)

R$^6$—A—R$^7$ (V)

in which

A represents optionally substituted alkylene,

R$^6$ represents amino or —SH,

R$^7$ represents amino, —COOR$^8$ or —CH(OR$^9$)$_2$ where

R$^8$ represents alkyl or hydrogen and

R$^9$ represents alkyl, if appropriate in the presence of a diluent and if appropriate in the presence of a reaction auxiliary, or c) ketones of the general formula (II)

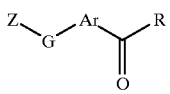
(II)

in which

Ar, G, R and Z are each as defined above are reacted with phosphorus compounds of the general formula (VI)

—R$^1$ (VI)

in which

R$^1$ is as defined above and

 represents —P(R$^{10}$)$_3$$^+$X$^-$ or represents —PO(OR$^{11}$)$_2$ where R$^{10}$ represents aryl or alkyl, R$^{11}$ represents alkyl and X represents halogen, if appropriate in the presence of a diluent and if appropriate in the presence of a reaction auxiliary, or d) thioamides of the general formula (VII)

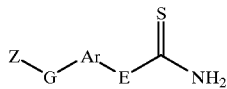
(VII)

in which

Ar, G, E and Z are each as defined above are reacted with halogenoalkyl compounds of the general formula (VIII)

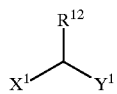
(VIII)

in which

R$^{12}$ represents hydrogen or alkyl,

X$^1$ represents halogen,

Y$^1$ represents cyano, alkylcarbonyl, arylcarbonyl, formyl, dialkoxyalkyl or alkoxycarbonyl, or with acetylene compounds of the formula (IX)

Y$^2$———Y$^3$ (IX)

in which

Y$^2$ represents alkoxycarbonyl and

Y$^3$ represents hydrogen, alkyl, aryl, alkylcarbonyl, arylcarbonyl or alkoxycarbonyl, if appropriate in the presence of a diluent and if appropriate in the presence of a reaction auxiliary.

If R$^2$ represents alkoxy, it is advantageous in some cases to prepare initially the corresponding hydroxy compounds (R$^2$=OH) by the method of process a) and to alkylate these compounds subsequently by conventional methods.

Finally, it has been found that the novel substituted heterocyclic compounds of the general formula (I) have a very strong fungicidal activity.

The compounds according to the invention may be present as mixtures of various possible isomeric forms, in particular of stereoisomers, such as, for example, E- and Z-isomers, and also as tautomers. Both the E- and the Z-isomers, and any mixtures of these isomers, and the possible tautomeric forms are claimed.

The invention preferably provides compounds of the formula (I) in which

Ar represents respectively optionally substituted phenylene or naphthylene, represents mono- or bicyclic heteroarylene having in each case 5 or 6 ring members or represents benzo-fused heteroarylene having 5 or 6 ring members, at least one of which in each case is oxygen, sulphur or nitrogen and one or two more are optionally nitrogen, the possible substituents preferably being selected from the list below:

halogen, cyano, nitro, amino, hydroxyl, formyl, carboxyl, carbamoyl, thiocarbamoyl, respectively straight-chain or branched alkyl, alkoxy, alkylthio, alkylsulphinyl or alkylsulphonyl having in each case 1 to 6 carbor atoms, respectively straight-chain or branched alkenyl, alkenyloxy or alkinyloxy having in each case 2 to 6 carbon atoms, respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, respectively straight-chain or branched halogenoalkenyl or halogenoalkenyloxy having in each case 2 to 6 carbon atoms and 1 to 13 identical or different halogen atoms, respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, alkylene or dioxyalkylene, each of which has 1 to 6 carbon atoms, is attached twice and is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms, E represents one of the groupings below:

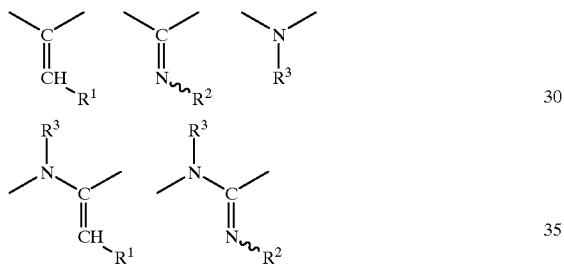

in which $R^1$ represents hydrogen, halogen, cyano or represents respectively optionally halogen-, cyano- or $C_1$-$C_4$-alkoxy-substituted alkyl, alkoxy, alkylthio, alkylamino or dialkylamino having in each case 1 to 6 carbon atoms in the alkyl moieties, $R^2$ represents hydrogen, amino, hydroxyl, cyano or represents respectively optionally halogen-, cyano- or $C_1$-$C_4$-alkoxy-substituted alkyl, alkoxy, alkylamino or dialkylamino having in each case 1 to 6 carbon atoms in the alkyl moieties, $R^3$ represents hydrogen, cyano, hydroxyl or represents respectively optionally halogen- or cyano-substituted alkyl, alkoxy, alkoxyalkyl, alkenyl or alkinyl having in each case up to 6 carbon atoms or represents respectively optionally halogen-, cyano-, $C_1$-$C_4$-alkyl- or $C_1$-$C_4$-alkoxy-substituted cycloalkyl or cycloalkylalkyl having 3 to 6 carbon atoms in the cycloalkyl moieties and optionally 1 to 4 carbon atoms in the alkyl moiety, G represents a single bond, represents oxygen or sulphur or represents respectively optionally halogen-, hydroxyl-, $C_1$-$C_4$-alkyl-, $C_1$-$C_4$-halogenoalkyl- or $C_3$-$C_6$-cycloalkyl-substituted alkanediyl, alkenediyl or alkinediyl having in each case up to 4 carbon atoms, or represents one of the groupings below:

—Q—CQ—, —CQ—Q—, —CH$_2$—Q—; —Q—CH$_2$-, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q—, —N(R$^5$)—CQ—Q—CH$_2$—, —Q—C(R$^4$)=N—O—CH$_2$—, —N(R$^5$)—C(R$^4$)=N—O—CH$_2$—, -O—CH$_2$—C(R$^4$)=N—O—CH$_2$—, —N=N—C(R$^4$)=N—O—CH$_2$—, —T—Ar$^1$— or —T—Ar$^1$—Q—, where n represents the numbers 0, 1 or 2, Q represents oxygen or sulphur, $R^4$ represents hydrogen, cyano, represents respectively optionally halogen-, cyano- or $C_1$-$C_4$-alkoxy-substituted alkyl, alkoxy, alkylthio, alkylamino or dialkylamino having in each case 1 to 6 carbon atoms in the alkyl moieties or represents respectively optionally halogen-, cyano-, carboxyl-, $C_1$-$C_4$-alkyl- or $C_1$-$C_4$-alkoxy-carbonyl-substituted cycloalkyl having 3 to 6 carbon atoms, and $R^5$ represents hydrogen, hydroxyl, cyano or represents optionally halogen-, cyano- or $C_1$-$C_4$-alkoxy-substituted alkyl having 1 to 6 carbon atoms or represents optionally halogen-, cyano-, carboxyl-, $C_1$-$C_4$-alkyl- or $C_1$-$C_4$-alkoxy-carbonyl-substituted cycloalkyl having 3 to 6 carbon atoms and $Ar^1$ represents phenylene, naphthylene or cycloalkylene, each of which is optionally mono- or polysubstituted by identical or different substituents, or represents heteroarylene or heterocycloalkylene having 3 to 7 ring members, at least one of which is oxygen, sulphur or nitrogen and one or two more are optionally nitrogen, the possible substituents preferably being selected from the list below:

halogen, cyano, nitro, amino, hydroxyl, formyl, carboxyl, carbamoyl, thiocarbamoyl; respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and;

cycloalkyl having 3 to 6 carbon atoms and

T represents a single bond, represents oxygen, sulphur, —CH$_2$—O—, —CH$_2$—S— or represents alkanediyl having 1 to 3 carbon atoms, R represents pyrrolyl, imidazolyl, pyrazolyl, 1,2,3-triazolyl, 1,2,4-triazolyl or tetrazolyl, each of which is attached via a carbon atom and each of which is optionally $C_1$-$C_4$-alkyl-substituted at a nitrogen atom, represents 1,2,5-oxadiazolyl, furyl, thienyl, 1,2-thiazolyl, 1,3-thiazolyl, 1,2,3-thiadiazolyl, 1,2,4-thiadiazolyl, 1,2,5-thiadiazolyl, 1,3,4-thiadiazolyl, pyridyl, pyrimidyl, pyrazyl, pyridazyl, 1,2,3-triazyl, 1,2,4-triazyl, 1,3,5-triazyl, partially or fully hydrogenated thiazolyl or thiazinyl, each of which is attached via a carbon atom and each of which is optionally alkyl-, alkoxy- or hydroxyl-substituted, represents optionally alkylidene-, arylalkylidene-, alkylcarbonylalkylidene-, arylcarbonylalkylidene- or alkoxycarbonylalkylidene-substituted 4-oxo-1,3-thiazol-2-yl, represents respectively optionally $C_1$–$C_4$-alkyl-substituted saturated heterocyclyl having 3 to 8 ring members, at least one ring member being oxygen and/or sulphur, or represents optionally $C_1$–$C_4$-alkyl-substituted 1,3-diazacycloalk-1-en-2-yl having 4 to 7 ring members, Z represents alkyl having 1 to 8 carbon atoms which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl or $C_1$–$C_4$-alkylsulphonyl (each of which may optionally be substituted by halogen);

represents respectively optionally halogen-substituted alkenyl or alkinyl having in each case up to 8 carbon atoms;

represents cycloalkyl having 3 to 6 carbon atoms which is optionally mono- or polysubstituted by identical or different substituents from the group consisting of halogen, cyano, carboxyl, phenyl (which is optionally halogen-, cyano-, $C_1$–$C_4$-alkyl-, $C_1$–$C_4$-halogenoalkyl-, $C_1$–$C_4$-alkoxy- or $C_1$–$C_4$-halogenoalkoxy-substituted), $C_1$–$C_4$-alkyl or $C_1$–$C_4$-alkoxy-carbonyl;

represents phenyl or naphthyl, each of which is optionally mono- or poly-substituted by identical or different substituents, or represents heterocyclyl having 3 to 7 ring members, at least one of which is oxygen, sulphur or nitrogen and one or two more are optionally nitrogen, the possible substituents preferably being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl or alkylsulphonyloxy having in each case 1 to 6 carbon atoms in the individual alkyl moieties;

alkylene or dioxyalkylene, each of which has 1 to 6 carbon atoms, is attached twice and is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl having in each case 3 to 7 ring members of which in each case 1 to 3 are identical or different hetero atoms—in particular nitrogen, oxygen and/or sulphur-, or a grouping

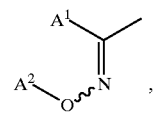

in which $A^1$ represents alkyl having 1 to 4 carbon atoms or cycloalkyl having 1 to 6 carbon atoms and $A^2$ represents optionally cyano-, $C_1$–$C_4$-alkoxy-, $C_1$–$C_4$-alkylthio-, $C_1$–$C_4$-alkyl- amino-, $C_1$–$C_2$-dialkylamino-, phenyl-, halogenophenyl-, methylphenyl-, trifluoromethylphenyl- or $C_1$–$C_2$-alkoxyphenyl-substituted alkyl having 1 to 4 carbon atoms, alkenyl or alkinyl having in each case 2 to 4 carbon atoms.

In the definitions, the saturated or unsaturated hydrocarbon chains, such as alkyl, alkanediyl, alkenyl or alkinyl are in each case, even in combination with hetero atoms, such as in alkoxy, alkylthio or alkylamino, straight-chain or branched.

Halogen generally represents fluorine, chlorine, bromine or iodine, preferably fluorine, chlorine or bromine, in particular fluorine or chlorine.

The invention relates in particular to compounds of the formula (I) in which

Ar represents respectively optionally substituted ortho-, meta- or para-phenylene, represents furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl (in particular pyridine-2,3 -diyl), pyrimidinediyl, pyridazinediyl, pyrazinediyl, 1,3,4-triazinediyl or 1,2,3-triazinediyl, the possible substituents being selected in particular from the list below:

fluorine, chlorine, cyano, methyl, ethyl, cyclopropyl, trifluoromethyl, methoxy, ethoxy, methylthio, methylsulphinyl or methylsulphonyl, E represents one of the groupings below:

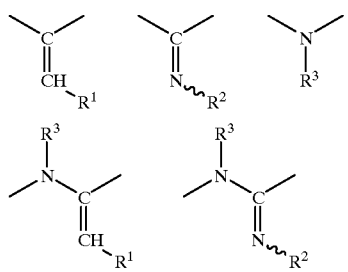

in which $R^1$ represents hydrogen, fluorine, chlorine, bromine, cyano or represents respectively optionally fluorine-, chlorine-, cyano-, methoxy- or ethoxy-substituted methyl, ethyl, propyl, methoxy, ethoxy, methylthio, ethylthio, methylamino, ethylamino or dimethylamino, $R^2$ represents hydrogen, amino, hydroxyl, cyano or represents respectively optionally fluorine-, chlorine-, cyano-, methoxy- or ethoxy-substituted methyl, ethyl, methoxy, ethoxy, methylamino, ethylamino or dimethylamino, $R^3$ represents hydrogen, cyano or represents respectively optionally fluorine-, chlorine- or cyano-substituted methyl, ethyl, n- or i-propyl, n-, i- or s-butyl, methoxy, ethoxy or methoxymethyl, represents allyl or propargyl or represents respectively optionally fluorine-, chlorine-, cyano-, methyl-, ethyl-, n- or i-propyl-, methoxy- or ethoxy-substituted cyclopropyl, cyclobutyl, cyclopentyl, cyclohexyl, cyclopropylmethyl, cyclobutylmethyl, cyclopentylmethyl or cyclohexylmethyl, G represents a single bond, represents oxygen or sulphur or represents respectively optionally fluorine-, chlorine-, bromine-, hydroxyl-, methyl-, ethyl-, n- or i-propyl-, trifluoromethyl-, cyclopropyl-, cyclobutyl-, cyclopentyl- or cyclohexyl-substituted methylene, dimethylene (ethane-1,2-diyl), ethene-1,2-(diyl, ethine-1,2-diyl or one of the groupings below:

—Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q—, —N(R$^5$)—CQ—Q—CH$_2$—, —Q—C(R$^4$)=N—O—CH$_2$—, —N(R$^5$)—C(R$^4$)=N—O—CH$_2$—, —O—CH$_2$—C(R$^4$)=N—O—CH$_2$-, —N=N—C(R$^4$)=N—O—CH$_2$-, —T—Ar$^1$—Q—, or —T—Ar$^1$—Q—, where n represents the numbers 0, 1 or 2, Q represents oxygen or sulphur, $R^4$ represents hydrogen, cyano, represents respectively optionally fluorine-, chlorine-, cyano-, methoxy- or ethoxy-substituted methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino or represents respectively optionally fluorine-, chlorine-, cyano-, carboxyl-, methyl-, ethyl-, n- or i-propyl-, methoxycarbonyl- or ethoxycarbonyl-substituted cyclopropyl, cyclobutyl, cyclopentyl or cyclohexyl, and $R^5$ represents hydrogen, hydroxyl, cyano or represents respectively optionally fluorine-, chlorine-, cyano-, methoxy- or ethoxy-substituted methyl, ethyl, n- or i-propyl, n-, i-, s- or t-butyl or represents respectively optionally fluorine-, chlorine-, cyano-, carboxyl-, methyl-, ethyl-, n- or i-propyl-, methoxycarbonyl- or ethoxy-carbonyl-substituted cyclopropyl, cyclobutyl, cyclopentyl or cyclohexyl, $Ar^1$ represents respectively optionally mono- to trisubstituted phenylene, naphthylene, furandiyl, thiophenediyl, oxazolediyl, isoxazolediyl, thiazolediyl, isothiazolediyl, 1,2,4-oxadiazolediyl, 1,3,4-oxadiazolediyl, 1,2,4-thiadiazolediyl, 1,3,4-thiadiazolediyl, pyridinediyl, pyrimidinediyl, pyridazinediyl, pyrazinediyl, 1,2,3-triazinediyl, 1,2,4-triazinediyl, 1,3,5-triazinediyl, oxiranediyl, oxetanediyl, tetrahydrofurandiyl, perhydropyranediyl or pyrrolidinediyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, (difluorochloromethoxy, trifluoroethoxy, difluoromethylthio, difluorochloromethylthio, trifluoromethylthio, trifluoromethylsulphinyl or trifluoiomethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl, ethoximinoethyl or cyclopropyl and T represents a single bond, represents oxygen, sulphur, —CH$_2$—O—, —CH$_2$—S—, methylene, ethylene or propylene and R represents pyrrolyl, imidazolyl, pyrazolyl, 1,2,3-triazolyl, 1,2,4-triazolyl or tetrazolyl, each of which is attached via a carbon atom and each of which is optionally methyl- or ethyl-substituted at a nitrogen atom, represents 1,2,5-oxadiazolyl, furyl, thienyl, 1,2-thiazolyl, 1,3-thiazolyl, 1,2,3-thiadiazolyl, 1,2,4-thiadiazolyl, 1,2,5-thiadiazolyl, 1,3,4-thiadiazolyl, pyridyl, pyrimidyl, pyrazyl, pyridazyl, 1,2,3-triazyl, 1,2,4-triazyl, 1,3,5-triazyl, partially or fully hydrogenated thiazolyl or thiazinyl, each of which is attached via a carbon atom and each of which is optionally methyl-, methoxy- or hydroxyl-substituted, represents optionally methylidene-, ethylidene-, benzylidene-, acetylmethylidene-, benzoylmethylidene-, ethoxycarbonylmethylidene- or methoxycaibonyl- methylidene-substituted 4-oxo-1,3-thiazol-2-yl, represents respectively optionally methyl- or ethyl-substituted saturated heterocyclyl having 3 to 8 ring members, one, two or three ring members being oxygen and/or sulphur, or represents imidazolidin-2-yl, tetrahydropyrimidin-2-yl or 4,5,6,7-tetrahydro-1H-1,3-diazepin-2-yl, each of which is optionally mono—, di- or trisubstituted by methyl or ethyl, Z represents methyl, ethyl, n- or i-propyl, n-, i-, s- or t-butyl, each of which is optionally mono- to pentasubstituted by fluorine, chlorine, bromide, cyano, hydroxyl, amino, methoxy, ethoxy, methylthio, ethylthio, methylsulphinyl, ethylsulphinyl, methylsulphonyl, ethylsulphonyl (each of which is optionally substituted by fluorine and/or chlorine);

represents allyl, crotonyl, 1-methyl-allyl, propargyl or 1-methyl-propargyl, each of which is optionally mono- to trisubstituted by fluorine, chlorine or bromide;

represents cyclopropyl, cyclobutyl, cyclopentyl or cyclohexyl, each of which is optionally mono- to hexasubstituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl;

represents respectively optionally mono- to trisubstituted phenyl, naphthyl, furyl, thienyl, oxazolyl, isoxazolyl, thiazolyl, isothiazolyl, 1,2,4-oxadiazolyl, 1,3,4-oxadiazolyl, 1,2,4-thiadiazolyl, 1,3,4-thiadiazolyl, pyridinyl, pyrimidinyl, pyridazinyl, pyrazinyl, 1,2,3-triazinyl, 1,2,4-triazinyl, 1,3,5-triazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethlylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphorlyloxy or ethylsulphonyloxy; trimethylene (propane-1,3-diyl), methylenedioxy orethylenedioxy, each of which is attached twice and each of which is optionally mono- or polysubstituted by identical or different substituents from the group consisting of fluorine, chlorine, methyl, trifluoromethyl, ethyl, n- or i-propyl, cyclopropyl, cyclobutyl, cyclopentyl or cyclohexyl, or a grouping

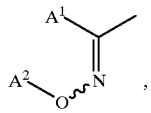

in which $A^1$ represents methyl, ethyl, n- or i-propyl, n-, i-, s- or t-butyl, cyclopropyl or cyclobutyl and $A^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, methylbenzyl, chlorobenzyl, fluorobenzyl, trifluoromethylbenzyl, benzoyl or chlorobenzoyl.

Very particular preference is given to compounds of the general formula (1) in which Ar represents ortho-phenylene, pyridine-2,3-diyl or thiophene-2,3-diyl, E represents one of the groupings below

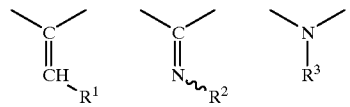

in which $R^1$ and $R^2$ each represent methoxy and $R^3$ represents hydrogen, cyano, methyl, ethyl, n- or i-propyl, methoxy, ethoxy or methoxymethyl, G represents oxygen or represents respectively optionally fluorine-, chlorine- or bromine-substituted dimethylene (ethane-1,2-diyl), ethene-1,2-diyl or one of the groupings below —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q—, —N(R$^5$)—CQ—Q—CH$_2$—, —Q—C(R$^4$)=N—O—CH$_2$—, —N(R$^5$)—C(R$^4$)=N—O—CH$_2$—, —O—CH$_2$—C(R$^4$)=N—O—CH$_2$-, —N=N—C(R$^4$)=N—O—CH$_2$—, —T—Ar$^1$ or —T—Ar$^1$—Q—, where n represents the numbers 0, 1 or 2, Q represents oxygen or sulphur, $R^4$ represents hydrogen, cyano, methyl, ethyl or cyclopropyl and $R^5$ represents hydrogen, methyl, ethyl or cyclopropyl, Ar$^1$ represents phenylene or pyridinediyl, each of which is optionally mono- to trisubstituted by identical or different substituents, represents respectively optionally monosubstituted pyrimidinediyl, pyridazinediyl, pyrazinediyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl or 1,3,4-oxadiazolediyl, the possible substituents preferably being selected from the list below:

fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl and T represents a single bond, represents oxygen, sulphur, —CH$_2$—O—, —CH$_2$—S—, methylene, ethylene or propylene and R represents pyrrolyl, imidazolyl, pyrazolyl, 1,2,3-triazolyl, 1,2,4-triazoyl or tetrazolyl, each of which is attached via a carbon atom and each of which is optionally methyl- or ethyl-substituted at a nitrogen atom, represents 1,2,5-oxadiazolyl, furyl, thienyl, 1,2-thiazolyl, 1,3-thiazolyl, 1,2,3-thiadiazolyl, 1,2,4-thiadiazolyl, 1,2,5-thiadiazolyl, 1,3,4-thiadiazolyl, pyridyl, pyrimidyl, pyrazyl, pyridazyl, 1,2,3-triazyl, 1,2,4-triazyl, 1,3,5-triazyl, partially or fully hydrogenated thiazolyl or thiazinyl, each of which is attached via a carbon atom and each of which is optionally methyl-, methoxy- or hydroxyl-substituted, represents optionally methylidene-, ethylidene-, benzylidene-, acetylmethylidene-, benzoylmethylidene-, ethoxycarbonylmethylidene- or methoxycarbonylmethylidene-substituted 4-oxo-1,3-thiazol-2-yl, represents respectively optionally methyl- or ethyl-substituted saturated heterocyclyl having 3 to 8 ring members, one, two or three ring members being oxygen and/or sulphur, or represents imidazolidin-2-yl, tetrahydropyrimidin-2-yl or 4,5,6,7-tetrahydro-1H-1,3-diazepin-2-yl, each of which is optionally mono—, di- or trisubstituted by methyl or ethyl, Z represents phenyl, 1,2,4-thiadiazolyl, 1,3,4-thiadiazolyl, 1,2,4-oxadiazolyl, 1,3,4-oxadiazolyl, pyridinyl, pyrimidinyl, pyridazinyl, pyrazinyl, 1,2,3-triazinyl, 1,2,4-triazinyl or 1,3,5-triazinyl, each of which is optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl or ethoxycarbonyl, methylenedioxy or ethylenedioxy, each of which is attached twice and each of which is optionally mono- to tetrasubstituted by identical or different substituents from the group consisting of fluorine, chlorine, methyl, trifluoromethyl and ethyl, or a grouping

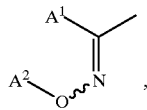

in which

A¹ represents methyl, ethyl, n- or i-propyl, n-, i-, s- or t-butyl, cyclopropyl or cyclobutyl and A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, methylbenzyl, chlorobenzyl, fluorobenzyl, trifluoromethylbenzyl, benzoyl or chlorobenzoyl.

An especially preferred group of compounds according to the invention are those compounds of the formula (I) in which Ar represents ortho-phenylene, pyridine-2,3-diyl or thiophene-2,3-diyl, E represents one of the groupings below

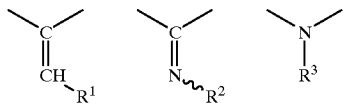

in which

R¹ and R² each represent methoxy,

R³ represents hydrogen , methyl or ethyl,

G represents —O—CH₂— and

R represents pyrrolyl, imidazolyl, pyrazolyl, 1,2,3-triazolyl, 1,2,4-triazolyl or tetrazolyl, each of which is attached via a carbon atom and each of which is optionally methyl- or ethyl-substituted at a nitrogen atom, represents 1,2,5-oxadiazolyl, furyl, thienyl, 1,2-thiazolyl, 1,3-thiazolyl, 1,2,3-thiadiazolyl, 1,2,4-thiadiazolyl, 1,2,5-thiadiazolyl, 1,3,4-thiadiazolyl, pyridyl, pyrimidyl, pyrazyl, pyridazyl, 1,2,3-triazyl, 1,2,4-triazyl, 1,3,5-triazyl, partially or fully hydrogenated thiazolyl or thiazinyl, each of which is attached via a carbon atom and each of which is optionally methyl-, methoxy- or hydroxyl-substituted, represents optionally methylidene-, ethylidene-, benzylidene-, acetylmethylidene-, benzoylmethylidene-, ethoxycarbonylmethylidene- or methoxycarbonylmethylidene-substituted 4-oxo-1,3-thiazol-2-yl, represents saturated heterocyclyl having 3 to 8 ring members, one, two or three ring members being oxygen and/or sulphur, which is optionally mono- or polysubstituted by methyl or ethyl, or represents imidazolidin-2-yl, tetrahydropyrimidin-2-yl or 4,5,6,7-tetrahydro-1H-1,3-diazepin-2-yl, each of which is optionally mono-, di- or trisubstituted by methyl or ethyl, z represents phenyl which is in each case optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl or ethoxycarbonyl, methylenedioxy or ethylenedioxy, each of which is attached twice and each of which is optionally mono- to tetrasubstituted by identical or different substituents from the group consisting of fluorine, chlorine, methyl, trifluoromethyl and ethyl, or a grouping

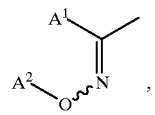

in which

A¹ represents methyl, ethyl, n- or i-propyl, n-, i-, s- or t-butyl, cyclopropyl or cyclobutyl and A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, methylbenzyl, chlorobenzyl, fluorobenzyl, trifluoromethylbenzyl, benzoyl or chlorobenzoyl.

A group of compounds according to the invention which is also especially preferred are those compounds of the formula (I)

in which

Ar represents ortho-phenylene, pyridine-2,3-diyl or thiophene-2,3-diyl,

E represents one of the groupings below

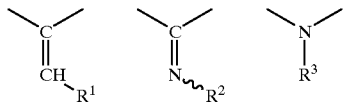

in which $R^1$ and $R^2$ each represent methoxy, $R^3$ represents hydrogen, methyl or ethyl, G represents —C($R^4$)=N—O—CH$_2$- where $R^4$ represents hydrogen, cyano, methyl, ethyl or cyclopropyl, R represents pyrrolyl, imidazolyl, pyrazolyl, 1,2,3-triazolyl, 1,2,4-triazolyl or tetrazolyl, each of which is attached via a carbon atom and each of which is optionally methyl- or ethyl-substituted at a nitrogen atom, represents 1,2,5-oxadiazolyl, furyl, thienyl, 1,2-thiazolyl, 1,3-thiazolyl, 1,2,3-thiadiazolyl, 1,2,4-thiadiazolyl, 1,2,5-thiadiazolyl, 1,3,4-thiadiazolyl, pyridyl, pyrimidyl, pyrazyl, pyridazyl, 1,2,3-triazyl, 1,2,4-triazyl, 1,3,5-triazyl, partially or fully hydrogenated thiazolyl or thiazinyl, each of which is attached via a carbon atom and each of which is optionally methyl-, methoxy- or hydroxyl-substituted, represents optionally methylidene-, ethylidene-, benzylidene-, acetylmethylidene-, benzoylmethylidene-, ethoxycarbonylmethylidene- or methoxycarbonyl- methylidene-substituted 4-oxo- 1,3-thiazol-2-yl, represents respectively optionally methyl- or ethyl-substituted saturated heterocyclyl having 3 to 8 ring members, one, two or three ring members being oxygen and/or sulphur, or represents imidazolidin-2-yl, tetrahydropyrimidin-2-yl or 4,5,6,7-tetrahydro-1H-1,3-diazepin-2-yl, each of which is optionally mono-, di- or trisubstituted by methyl or ethyl, Z represents phenyl, pyridyl or pyrimidyl, each of which is optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethlyl, or represents methylenedioxy or ethyienedioxy, each of which is attached twice and each of which is optionally mono- to tetrasubstituted by identical or different substituents from the group consisting of fluorine, chlorine, methyl, trifluoromethyl or ethyl.

A group of compounds according to the invention which is furthermore especially preferred are those compounds of the formula (I)

in which

Ar represents ortho-phenylene,

E represents one of the groupings below

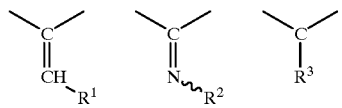

in which $R^1$ and $R^2$ each represent methoxy, $R^3$ represents hydrogen, methyl or ethyl, G represents —T—Ar$^1$—Q— where Q represents oxygen or sulphur, Ar$^1$ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents from the group consisting of fluorine, chlorine, cyano, methyl, cyclopropyl, methoxy, methylthio, trifluoromethyl, difluoromethoxy, trifluoromethoxy and difluorochloromethoxy, T represents a single bond, represents oxygen, sulphur, —CH$_2$—O—, —CH$_2$—S—, methylene, ethylene or propylene and R represents pyrrolyl, imidazolyl, pyrazolyl, 1,2,3-triazolyl, 1,2,4-triazolyl or tetrazolyl, each of which is attached via a carbon atom and each of which is optionally methyl- or ethyl-substituted at a nitrogen atom, represents 1,2,5-oxadiazolyl, furyl, thienyl, 1,2-thiazolyl, 1,3-thiazolyl, 1,2,3-thiadiazolyl, 1,2,4-thiadiazolyl, 1,2,5-thiadiazolyl, 1,3,4-thiadiazolyl, pyridyl, pyrimidyl, pyrazyl, pyridazyl, 1,2,3-triazyl, 1,2,4-triazyl, 1,3,5-triazyl, partially or fully hydrogenated thiazolyl or thiazinyl, each of which is attached via a carbon atom and each of which is optionally methyl-, methoxy- or hydroxyl-substituted, represents optionally methylidene-, ethylidene-, benzylidene-, acetylmethylidene-, benzoylmethylidene-, ethoxycarbonylmethylidene- or methoxycarbonylmethylidene-substituted 4-oxo-1,3-thiazol-2-yl, represents respectively optionally methyl- or ethyl-substituted saturated heterocyclyl having 3 to 8 ring members, one, two or three ring members being oxygen and/or sulphur, or represents imidazolidin-2-yl, tetrahydropyrimidin-2-yl or 4,5,6,7-tetrahydro-1H-1,3-diazepin-2-yl, each of which is optionally mono-, di- or trisubstituted by methyl or ethyl, Z represents phenyl, pyridyl or thienyl, each of which is optionally mono- to trisubstituted by identical or different substituents from the group consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy, difluorochloromethoxy, trifluoroethoxy and trifluoromethoxy, and methylenedioxy and ethylenedioxy, each of which is attached twice and each of which is optionally mono- or polysubstituted by identical or different substituents from the group consisting of fluorine, chlorine, methyl, trifluoromethyl or ethyl.

The abovementioned general or preferred radical definitions apply both to the end products of the formula (I) and, correspondingly, to the starting materials or intermediates required in each case for the preparation.

These radical definitions can be combined with each other as desired, that is to say combinations between the stated ranges of preferred compounds are also possible.

Examples of the compounds according to the invention are listed in Tables 1 to 40:

TABLE 1
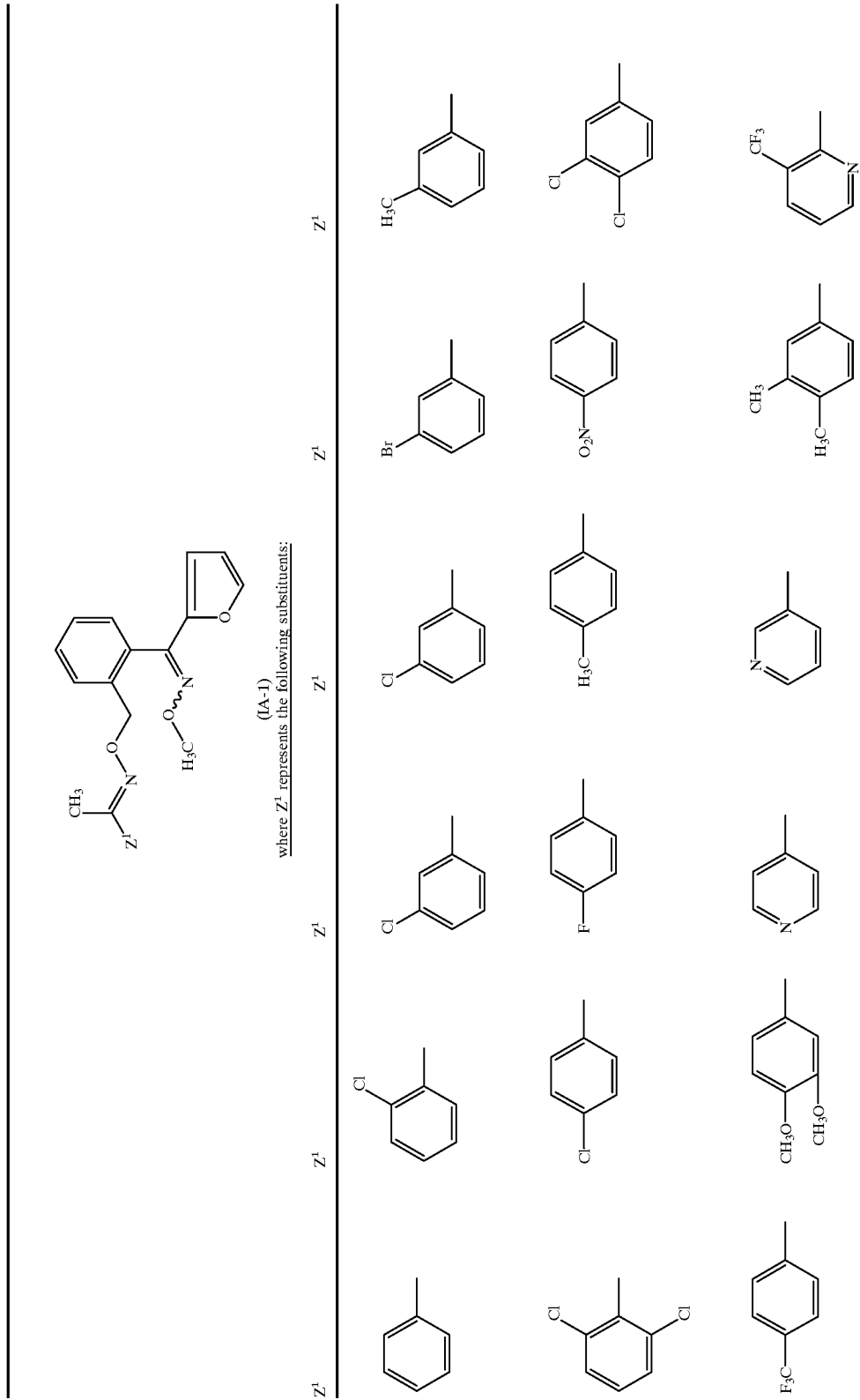
where $Z^1$ represents the following substituents:

TABLE 1-continued

TABLE 2

(IA-2)

where Z¹ represents the substituents listed in Table 1.

TABLE 3

(IA-3)

where Z¹ represents the substituents listed in Table 1.

TABLE 4

(IA-4)

where Z¹ represents the substituents listed in Table 1.

TABLE 5

(IA-5)

where Z¹ represents the substituents listed in Table 1.

TABLE 6

(IA-6)

where Z¹ represents the substituents listed in Table 1.

TABLE 7

(IA-7)

where Z¹ represents the substituents listed in Table 1.

TABLE 8

(IA-8)

where Z¹ represents the substituents listed in Table 1.

TABLE 9

(IA-9)

where Z¹ represents the substituents listed in Table 1.

TABLE 10
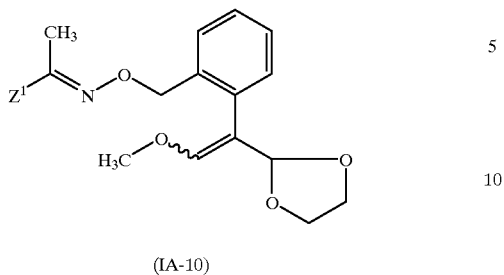
(IA-10)
where $Z^1$ represents the substituents listed in Table 1.

TABLE 11
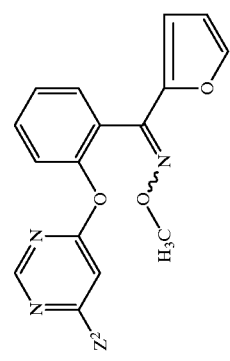
(IB-1)
where $Z^2$ represents the following substituents:

TABLE 11-continued (IB-1)

where $Z^2$ represents the following substituents:

TABLE 11-continued (IB-1)
where Z² represents the following substituents:

TABLE 11-continued
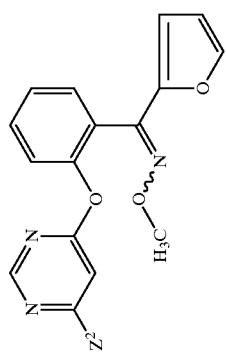
(IB-1)
where $Z^2$ represents the following substituents:
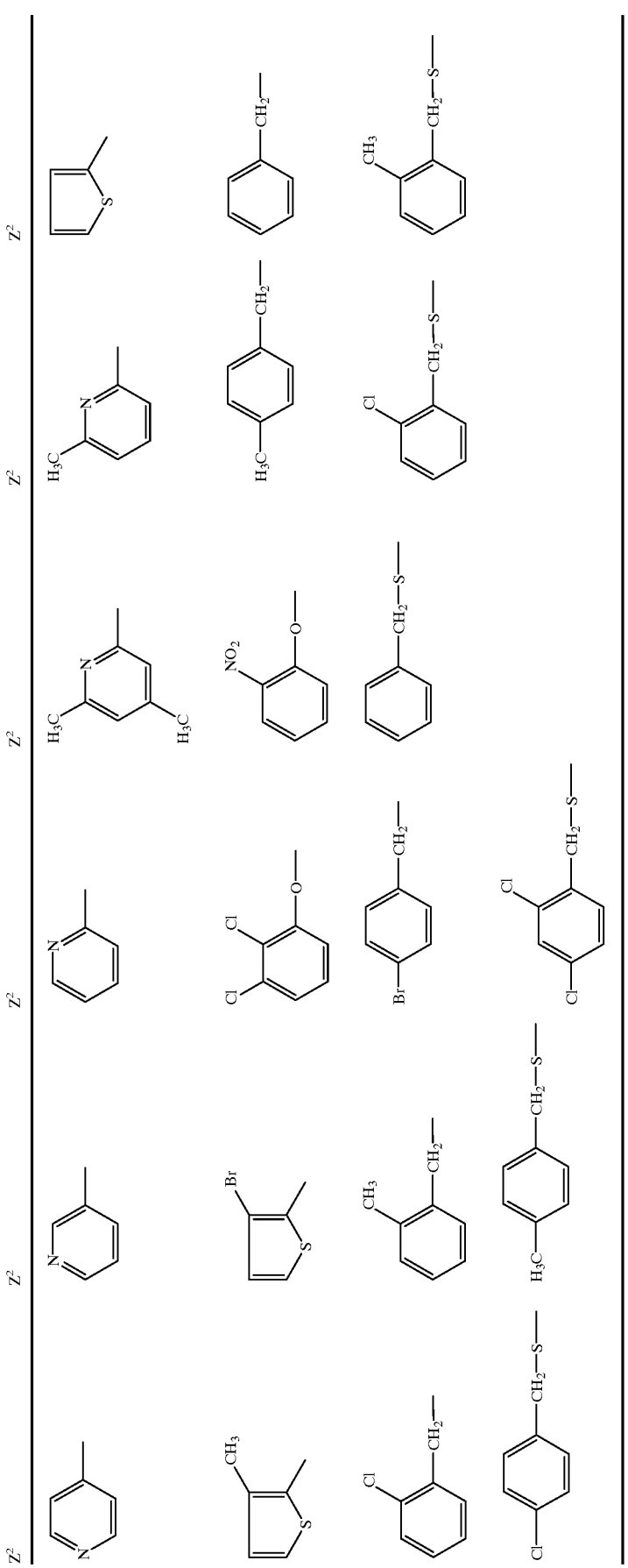

TABLE 12

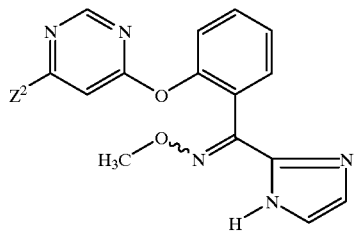

(IB-2)

where $Z^2$ represents the substituents listed in Table 11.

TABLE 13

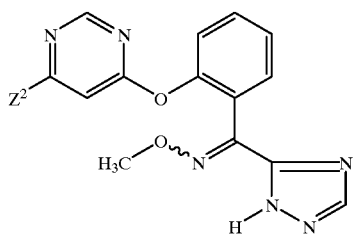

(IB-3)

where $Z^2$ represents the substituents listed in Table 11.

TABLE 14

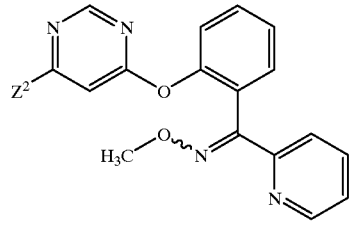

(IB-4)

where $Z^2$ represents the substituents listed in Table 11.

TABLE 15

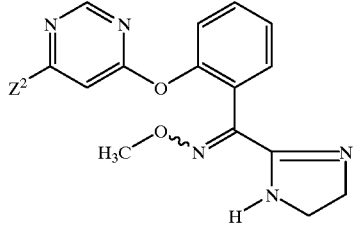

(IB-5)

where $Z^2$ represents the substituents listed in Table 11.

TABLE 16

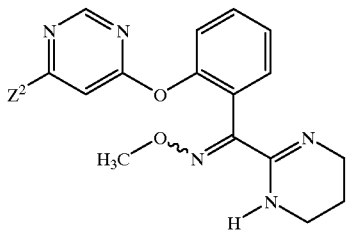

(IB-6)

where $Z^2$ represents the substituents listed in Table 11.

TABLE 17

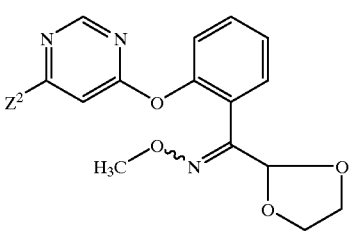

(IB-7)

where $Z^2$ represents the substituents listed in Table 11.

TABLE 18

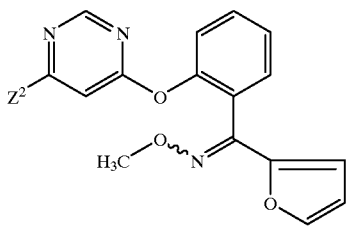

(IB-8)

where $Z^2$ represents the substituents listed in Table 11.

TABLE 19

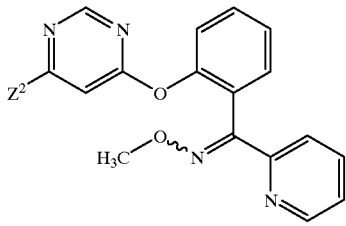

(IB-9)

where $Z^2$ represents the substituents listed in Table 11.

TABLE 20

(IB-10)

where Z² represents the substituents listed in Table 11.

TABLE 21

(IC-1)

where Z² represents the substituents listed in Table 11.

TABLE 22

(IC-2)

where Z² represents the substituents listed in Table 11.

TABLE 23

(IC-3)

where Z² represents the substituents listed in Table 11.

TABLE 24

(IC-4)

where Z² represents the substituents listed in Table 11.

TABLE 25

(IC-5)

where Z² represents the substituents listed in Table 11.

TABLE 26

(IC-6)

where Z² represents the substituents listed in Table 11.

TABLE 27

(IC-7)

where Z² represents the substituents listed in Table 11.

TABLE 28
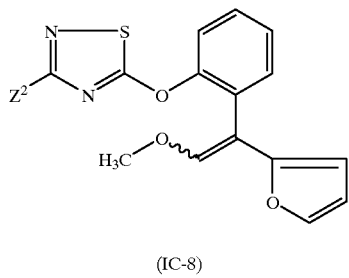
(IC-8)
where Z² represents the substituents listed in Table 11.
TABLE 29
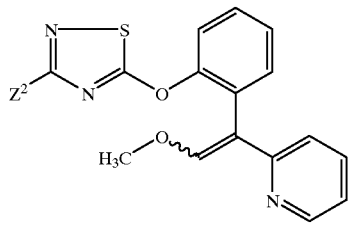
(IC-9)
where Z² represents the substituents listed in Table 11.
TABLE 30
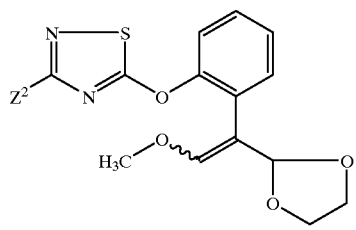
(IC-10)
where Z² represents the substituents listed in Table 11.

TABLE 31
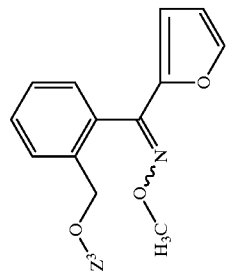
(ID-1)
where Z³ represents the following substituents:
| Z³ | Z³ | Z³ | Z³ | Z³ | Z³ |
|---|---|---|---|---|---|
| phenyl | 2-CH₃-phenyl | 2-C₂H₅-phenyl | 2-F-phenyl | 2-Cl-phenyl | 2-Br-phenyl |
| 2-CF₃-phenyl | 2-OCH₃-phenyl | 2-OCHF₂-phenyl | 3-Cl-phenyl | 3-CH₃-phenyl | 3-CF₃-phenyl |
| 4-CH₃-phenyl | 4-F-phenyl | 4-Cl-phenyl | 4-CH₃-3-CH₃(o)-phenyl | 2,4-Cl-phenyl | 2-CH₃-5-Cl-phenyl |
| 2,4-F-phenyl | 3-Cl-4-CH₃-phenyl | 3-CF₃O-2-Cl-phenyl | 2,3-Cl-phenyl | 2-CH₃-3-CH₃-phenyl | 2,4-Cl-phenyl |

TABLE 31-continued
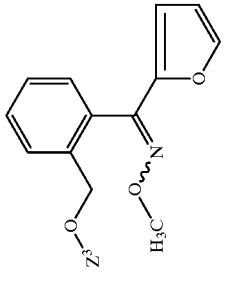
(ID-1)
where Z³ represents the following substituents:
| Z³ | Z³ | Z³ | Z³ | Z³ | Z³ |
|---|---|---|---|---|---|
| 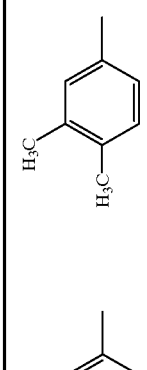 |  |  |  | 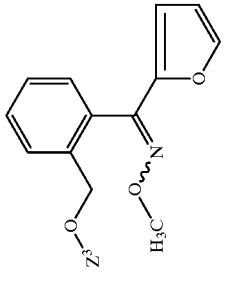 | 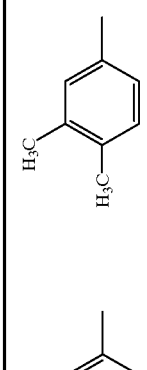 |
| |  |  | | | |

TABLE 32

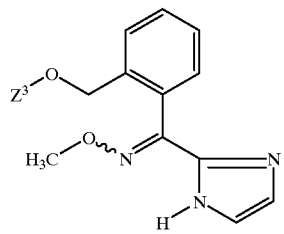

(ID-2)

where Z³ represents the substituents listed in Table 31.

TABLE 33

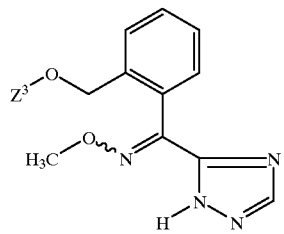

(ID-3)

where Z³ represents the substituents listed in Table 31.

TABLE 34

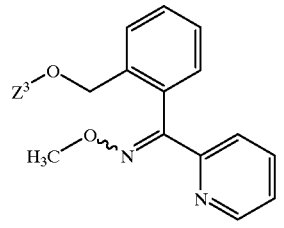

(ID-4)

where Z³ represents the substituents listed in Table 31.

TABLE 35

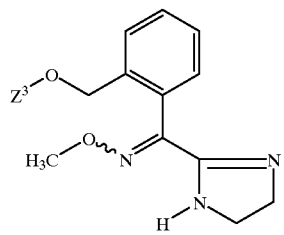

(ID-5)

where Z³ represents the substituents listed in Table 31.

TABLE 36

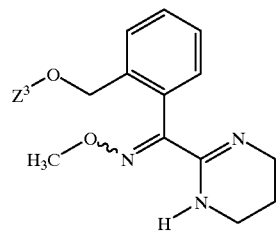

(ID-6)

where Z³ represents the substituents listed in Table 31.

TABLE 37

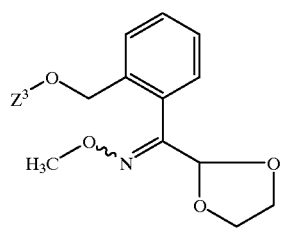

(ID-7)

where Z³ represents the substituents listed in Table 31.

TABLE 38

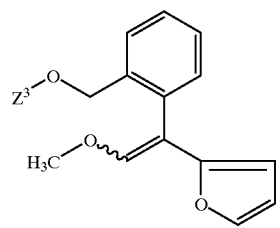

(ID-8)

where Z³ represents the substituents listed in Table 31.

TABLE 39

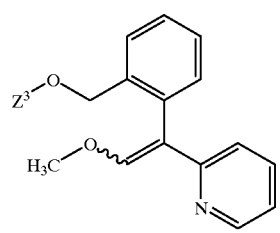

(ID-9)

where Z³ represents the substituents listed in Table 31.

TABLE 40

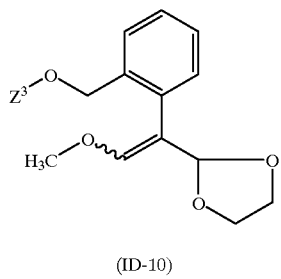

(ID-10)

where $Z^3$ represents the substituents listed in Table 31.

The ketones required as starting materials to carry out the process a) according to the invention are defined in a general way by the formula (II). In this formula (II), Ar, G, R and Z each preferably or in particular have those meanings already given in connection with the description of the compounds of the formula (I) according to the invention as preferred or as particularly preferred for Ar, G, R and Z.

The ketones of the formula (II) have not been disclosed; as novel compounds, they form part of the subject matter of the present application.

The ketones of the formula (II) are obtained (process a-a1)) when carboxamides of the general formula (X)

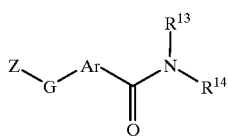

(X)

in which

Ar, G and Z are each as defined above and $R^{13}$ and $R^{14}$ are identical or different and each represent alkyl, or, together with the nitrogen atom to which they are attached, represent an optionally substituted ring in which optionally one or two further ring members are hetero atoms, are reacted with an organometallic compound of the formula (XI)

R—M (XI)

in which

R is as defined above and

M represents lithium or —Mg—$X^2$ where $X^2$ is chlorine, bromine, iodine or R, if appropriate in the presence of a diluent, preferably an aliphatic, alicyclic or aromatic hydrocarbon, such as, for example, petroleum ether, hexane, heptane, cyclohexane, methylcyclohexane, benzene, toluene, xylene or decalin; or of an ether, such as, for example, diethyl ether, diisopropyl ether, methyl t-butyl ether, methyl t-amyl ether, dioxane, tetrahydrofuran, 1,2-dimethoxyethane, 1,2-diethoxyethane or anisole, at temperatures from −80 to +50, preferably −80 to +25, °C.

The amides required as starting materials to carry out the process a-a1) according to the invention are defined in a general way by the formula (X). In this formula (X), Ar G and Z each preferably or in particular have those meanings already given in connection with the description of the compounds of the formula (I) according to the invention as preferred or as particularly preferred for Ar, G and Z. $R^{13}$ and $R^{14}$ are identical or different and represent alkyl, preferably methyl, ethyl, n- or i-propyl, or, together with the nitrogen atom to which they are attached, represent a 3-, 4-, 5-, 6- or 7-membered ring which is optionally mono- or polysubstituted by alkyl, preferably methyl or ethyl, in which optionally one or two further ring members are hetero atoms, preferably nitrogen, oxygen or sulphur.

Furthermore, it was found that the carboxamides of the formula (X) also have a very strong fungicidal activity.

Some of the carboxamides of the formula (X) are known and/or can be prepared by known methods (cf. for example DE-A 2806562 or WO-A 9422844).

Novel, and also part of the subject matter of the present application, are the carboxamides of the formula (Xa)

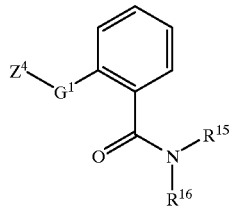

(Xa)

in which $G^1$ represents —O—$CH_2$—, —C($CH_3$)=N—O— or —$T^1$—$Ar^2$—O— where $Ar^2$ represents heteroarylene which is optionally mono-substituted by halogen, $T^1$ represents a single bond, represents oxygen, sulphur, —$CH_2$—O—, —$CH_2$—S— or represents optionally substituted alkanediyl and $Z^4$ represents optionally substituted phenyl, $R^5$ represents hydrogen or alkyl, $R^{16}$ represents optionally cycloalkyl-, hydroxyl- or alkoxy-substituted alkyl or alkenyl, or represents optionally alkyl-substituted cycloalkyl or represents hydroxyl or alkoxy, or $R^{15}$ and $R^{16}$, together with the nitrogen atom to which they are attached, represent an optionally alkyl-substituted heterocyclic ring which may contain an additional oxygen or nitrogen atom.

The carboxamides of the formula (Xa) are obtained (process a-a2) when acid derivatives of the formula (XII)

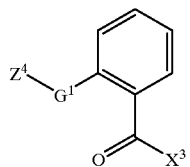

(XII)

in which $G^1$ and $Z^4$ are each as defined above and $X^3$ represents halogen, hydroxyl, alkoxy, alkylthio or —O—CO—Ar—G—Z are reacted with an amine of the general formula (XIII)

XIII in which
R¹⁵ and R¹⁶ are each as defined above, if appropriate in the presence of a diluent, preferably an aliphatic, alicyclic or aromatic hydrocarbon, such as, for example, petroleum ether or toluene; a halogenated hydrocarbon, such as, for example, dichloromethane; an ether, such as, for example, tetrahydrofuran, a nitrile, such as acetonitrile, an amide, such as, N,N-dimethylformamide, an ester, such as ethyl acetate; a sulphoxide, such as dimethyl sulphoxide; a sulphone, such as sulpholane, or an amine, such as pyridine, mixtures of the above diluents with water or pure water at temperatures between −20° C. and +200° C., preferably at temperatures between 0° C. and 150° C., and, if appropriate, in the presence of an acid acceptor, preferably a customary inorganic or organic base such as, for example, sodium hydroxide, triethylamine or pyridine.

Also preferably part of the subject-matter of the present application are carboxamides of the formula (Xa) in which
G¹ represents —O—CH₂—, —C(CH₃)=N—O— or —T¹Ar²—O— where
Ar² represents 1,2,4-oxadiazolediyl, 1,3,4-oxadiazolediyl, 1,2,4-thiadiazolediyl, 1,3,4-thiadiazolediyl or represents pyrimidinediyl or 1,3,5-triazinediyl, each of which is optionally monosubstituted by halogen,
T¹ represents a single bond, represents oxygen, sulphur, —CH₂—, —CH₂—CH₂-, —CH₂—O— or —CH₂—S— and
Z⁴ represents phenyl which is in each case optionally mono- to trisubstituted by identical or different substituents, the possible substituents preferably being selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl,
methylenedioxy or ethylenedioxy, each of which is attached twice and each of which is optionally mono- to tetrasubstituted by identical or different substituents from the group consisting of fluorine, chlorine, methyl, trifluoromethyl or ethyl,
or a grouping

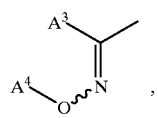

in which
A³ represents methyl, ethyl, n- or i-propyl, n-, i-, s- or t-butyl, cyclopropyl or cyclobutyl and A⁴ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, methylbenzyl, chlorobenzyl, fluorobenzyl, trifluoromethylbenzyl, benzoyl, chlorobenzoyl or fluorobenzoyl, R⁵ represents hydrogen or methyl, ethyl, n- or i-propyl, n-, i-, s- or t-butyl, R¹⁶ represents methyl, cyclopropylmethyl, hydroxyl, methoxy, ethoxy or optionally carboxyl-, hydroxyl- or methoxy-substituted ethyl, n- or i-propyl, n-, i-, s- or t-butyl, 1-, 2- or 3-pentyl, 1-, 2- or 3-hexyl, 1-, 2-, 3- or 4-heptyl, allyl, or represents optionally methyl-substituted cyclopropyl, cyclobutyl, cyclopentyl or cyclohexyl, or R¹⁵ and R¹⁶, together with the nitrogen atom to which they are attached, represent a pyrrolidine, piperidine, N'-methylpiperazine or morpholine ring.

The acid derivatives required as starting materials to carry out the process a-a2) according to the invention for the preparation of the carboxamides of the formula (Xa) are defined in a general way by the formula (XII). In this formula (XII), G¹ and Z⁴ each preferably or in particular have those meanings already given in connection with the description of the compounds of the formula (I) according to the invention as preferred or as particularly preferred for G¹ and Z⁴. X³ represents halogen, preferably chlorine; hydroxyl; alkoxy, preferably methoxy or ethoxy; alkylthio, preferably methylthio, ethylthio or benzylthio or represents —O—CO—(o—C₆H₄)-G¹-Z⁴.

The acid derivatives of the formula (XII) are known and/or can be prepared b processes known per se (cf. for example EP-A 49371 1).

The amines further required as starting materials to carry out the process a-a2) according to the invention for the preparation of the carboxamides of the formula (Xa) are defined in a general way by the formula (XIII). In this formula (XIII), R¹⁵ and R¹⁶ each preferably or in particular have those meanings already given in connection with the description of the carboxamides of the formula (Xa) as preferred or as particularly preferred for R¹⁵ and R¹⁶.

The amines of the formula (XIII) are known chemicals for synthesis.

The organometallic compounds further required as starting materials to carry out the process a-a1) according to the invention for the preparation of the ketones of the formula (II) are defined in a general way by the formula (XI). In this formula (XI), R preferably or in particular has those meanings already given in connection with the description of the compounds of the formula (I) according to the invention as preferred or as particularly preferred for R. M represents lithium or —Mg—X² where X² represents chlorine, bromine, iodine or R.

The organometallic compounds of the formula (XI) are known and/or can be prepared by processes known per se (cf. for example J. Org. Chem., 1962, 27, 1216; Synth. Comm., 1982, 12, 231; J. Org. Chem. 1971, 36, 1053; J. Org. Chem. 1980, 45 (20), 4040; J. C. S. Chem. Commun., 1983, 49; J. Org. Chem. 1985, 50, 662; Angew. Chem., Int. Ed. 1965, 4, 1077; Chem. Ber., 1974, 107, 367; Chem. Ber. 1992, 125, 7, 1641; Chem. Pharm. Bull., 1986, 34, 4916; J. Am. Chem. Soc. 1989, 111 (4), 1381–1392).

If R represents pyrrolyl, imidazolyl, pyrazolyl, triazolyl or tetrazolyl, it is advantageous to protect the NH grouping by reaction with an orthoformate and to remove the protecting group after the above-described reaction by conventional methods. (Cf. also the Preparation Examples).

The ketones of the formula (II) are also obtained (process a-b1)) when carbonitriles of the general formula (XIV)

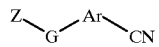

(XIV)

in which
Ar, G and Z are each as defined above,
are reacted with an organometallic compound of the formula (XI) already described above in connection with the process a-a1) according to the invention for the preparation of the ketones of the formula (II),
if appropriate in the presence of a diluent, preferably an aliphatic, alicyclic or aromatic hydrocarbon, such as, for example, petroleum ether, hexane, heptane, cyclohexane, methylcyclohexane, benzene, toluene, xylene or decalin; or of an ether, such as, for example, diethyl ether, diisopropyl ether, methyl t-butyl ether, methyl t-amyl ether, dioxane, tetrahydrofuran, 1,2-dimethoxyethane, 1,2-diethoxyethane or anisole, at temperatures from −80 to +50, preferably −80 to +25, °C.

The carbonitriles required as starting materials to carry out the process a-b1) according to the invention are defined in a general way by the formula (XIV). In this formula (XIV), Ar, G and Z each preferably or in particular have those meanings already given in connection with the description of the compounds of the formula (I) according to the invention as preferred or as particularly preferred for Ar, G and Z.

The carbonitriles of the formula (XIV) are known and/or can be prepared by processes known per se (cf. for example EP-A 278 595 or J. Org. Chem. (1982), 47(8), 1546–55).

The ketones of the formula (II) are also obtained (process a-c1)) when halogen compounds of the general formula (XV)

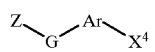

(XV)

in which
Ar, G and Z are each as defined above and
$X^4$ represents halogen
are converted, into the corresponding organometallic derivatives using for example, magnesium turnings or butyl-lithium in a conventional manner, and the organometallic derivatives are then reacted with a nitrile of the formula (XVI)

(XVI)

in which
R is as defined above
25 or with an amide of the formula (XVII)

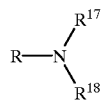

(XVII)

in which
R is as defined above and
$R^7$ and $R^{18}$ are identical or different and each represent alkyl, or, together with the nitrogen atom to which they are attached, represent an optionally substituted ring in which optionally one or two further ring members are hetero atoms,
if appropriate in the presence of a diluent, preferably an aliphatic, alicyclic or aromatic hydrocarbon, such as, for example, petroleum ether, hexane, heptane, cyclohexane, methylcyclohexane, benzene, toluene, xylene or decalin; or an ether, such as, for example, diethyl ether, diisopropyl ether, methyl t-butyl ether, methyl t-amyl, ether, dioxane, tetrahydrofuran, 1,2-dimethoxyethane, 1,2-diethoxyethane or anisole, at temperatures from −80 to +50, preferably −80 to +25, °C.

The halogen compounds required as starting materials to carry out the process a-c1) according to the invention are defined in a general way by the formula (XV). In this formula (XV), Ar, G and Z each preferably or in particular have those meanings already given in connection with the description of the compounds of the formula (I) according to the invention as preferred or as particularly preferred for Ar, G and Z.

The halogen compounds of the formula (XV) are known and/or can be prepared by processes known per se (cf. for example Synthesis 1981, (2), 117; EP-A 525 516, EP-A 585 751, Bull. Korean Chem. Soc. (1989), 10(4), 397–400; Synthesis (1987)., (10), 951–3).

The nitriles or amides further required as starting materials to carry out the process a-c1) according to the invention for the preparation of the ketones of the formula (II) are defined in a general way by the formulae (XVI) and (XVII), respectively. In these formulae (XVI) and (XVII), R preferably or in particular has those meanings already given in connection with the description of the compounds of the formula (I) according to the invention as preferred or as particularly preferred for R. In formula (XVII), $R^{17}$ and $R^{18}$ are identical or different and each represent alkyl, preferably methyl, ethyl, n- or i-propyl, or, together with the nitrogen atom to which they are attached, represent a three-, four-, five-, six- or seven-membered ring which is optionally mono- or polysubstituted by alkyl, preferably methyl or ethyl, and in which optionally one or two further ring members are hetero atoms, preferably nitrogen, oxygen or sulphur.

The nitriles of the formula (XVI) and the amides of the formula (XVII) are known organic chemicals for synthesis.

The ketones of the formula (II) can also be obtained when aromatic compounds of the general formula (XVIII)

(XVIII)

in which
Ar, G and Z are each as defined above,
are reacted with an acyl chloride of the formula (XIX)

(XIX)

in which
R is as defined above
by customary methods (Friedel-Crafts reaction), cf. for example DE-A 25557956,
or
when the halogen compounds of the general formula (XV) described further above are converted into the corresponding organometallic derivatives using, for example, magnesium turnings or butyllithium in a conventional manner, and the organometallic derivatives are then reacted with an aldehyde of the formula (XX)

        (XX)

in which

R is as defined above in a conventional manner (for example "Grignard reaction") to give the alcohols of the formula (XXI)

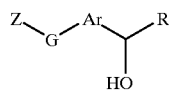        (XXI)

in which

Ar, G, R and Z are each as defined above (cf. also for example DE-A 2 557 956), and these are then oxidized by conventional methods.

The nitriles required as starting materials to carry out the process b) according to the invention are defined in a general way by the formula (IV). In this formula (IV), Ar, E, G and Z each preferably or in particular have those meanings already given in connection with the description of the compounds of the formula (I) according to the invention as preferred or as particularly preferred for Ar, E, G and Z.

Some of the nitrites of the formula (IV) are known and/or can be prepared by known processes (cf. for example EP-A 528 681, see also the Preparation Examples).

Novel, and also part of the subject-matter of the present invention, are the nitriles of the general formula (IVa)

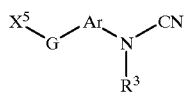        (IVa)

in which

Ar, G, $R^3$ and Z are each as defined above.

The nitriles of the general formula (IVa) are obtained (process b-1) when halogenomethyl compounds of the formula (XXII)

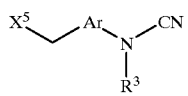        (XXII)

in which

Ar and $R^3$ are each as defined above and $X^5$ represents halogen are reacted with a hydroxyl compound of the general formula (XXIII), (XXIV) or (XXV)

        (XXIII)

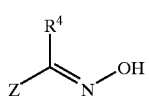        (XXIV)

(XXV)

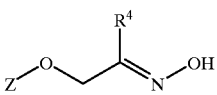

in which $R^4$ and Z are each as defined above, if appropriate in the presence of a diluent, preferably an ether, such as tetrahydrofuran, a ketone, such as acetone, a nitrile, such as acetonitrile, an amide, such as N,N-dimethylformamide or a sulphoxide, such as dimethyl sulphoxide, and, if appropriate, in the presence of an acid acceptor, preferably an alkali metal hydride, hydroxide or carbonate, such as, for example, sodium hydride, sodium hydroxide or potassium carbonate, at temperatures from −20 to 120° C.

The halogenomethyl compounds required as starting materials to carry out the process b-1) according to the invention are defined in a general way by the formula (XXII). In this formula (XXII), Ar and $R^3$ each preferably or in particular have those meanings already given in connection with the description of the compounds of the formula (I) according to the invention as preferred or as particularly preferred for Ar and $R^3$.

The halogenomethyl compounds of the formula (XXII) have not been disclosed; as novel compounds, they also form part of the subject-matter of the present application.

The halogenomethyl compounds of the formula (XXII) are obtained (process b-2) when methyl compounds of the general formula (XXVI)

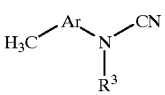        (XXVI)

in which

Ar and $R^3$ are each as defined above are reacted with a conventional halogenating agent, such as, for example, bromine, chlorine, N-bromosuccinimide or N-iodosuccinimide, if appropriate in the presence of a diluent, preferably an aliphatic, alicyclic or aromatic hydrocarbon, such as, for example, hexane or benzene, or a halogenated hydrocarbon, such as, for example, carbon tetrachloride, and, if appropriate, in the presence of a free radical initiator, such as, for example, benzoyl peroxide or azodiisobutyronitrile, if appropriate under irradiation with UV light, at a temperature from −20 to 120° C.

The methyl compounds required as starting materials to carry out the process b-2) according to the invention are defined in a general way by the formula (XVI). In this formula (XVI), Ar and $R^3$ each preferably or in particular have those meanings already given in connection with the description of the compounds of the formula (I) according to the invention as preferred or as particularly preferred for Ar and $R^3$.

The methyl compounds of the formula (XXVI) are known and/or can be prepared by processes known per se (cf. Org. Synth. Coll. Vol. 1955, 608).

The hydroxyl compounds further required as starting materials to carry out the process b-1) according to the invention are each defined in a general way by the formulae (XXIII), (XXIV) or (XXV). In these formulae (XXIII), (XXIV) or (XXV), $R^4$ and Z each preferably or in particular have those meanings already given in connection with the description of the compounds of the formula (1) according to the invention a preferred or as particularly preferred for $R^4$ and Z.

The hydroxyl compounds of the formulae (XXIII), (XXIV) or (XXV) are known chemicals for synthesis and/or can be prepared by processes known per se.

The bifunctional alkylene compounds further required as starting materials to carry out process b) according to the invention are defined in a general way by the formula (V). If this formula (V), $R^6$ represents amino or —SH, $R^7$ represents amino, —COOR$^8$ or —CH(OR$^9$)$_2$ where $R^8$ represents hydrogen or alkyl, preferably methyl or ethyl, and $R^9$ represents alkyl, preferably methyl or ethyl, and A represents optionally substituted straight-chain or branched alkylene. If $R^6$ and $R^7$ both represent amino, A preferably represents straight-chain or branched alkylene having 2 to 10 carbon atoms, in particular ethane-1,2-diyl, propane-1,3-diyl or butane-1,4-diyl, each of which is optionally mono-, di- or trisubstituted by methyl or ethyl. If $R^7$ represents —COOR$^8$ or —CH(OR$^9$)$_2$, A preferably represents straight-chain or branched alkylene having 1 to 8 carbon atoms, in particular methylene, ethane-1,2-diyl or propane-1,3-diyl, each of which is optionally mono-, di- or trisubstituted by methyl or ethyl.

The bifunctional alkylene compounds of the formula (V) are known chemicals for synthesis.

The ketones of the formula (II) required as starting materials to carry out the process c) according to the invention have already been described further above in the description of process a) according to the invention.

The phosphorus compounds required as starting materials to carry out the process c) according to the invention are defined in a general way by the formula (VI). In this formula (VI), $R^1$ preferably or in particular has those meanings already given in connection with the description of the compounds of the formula (I) according to the invention as preferred or as particularly preferred for $R^1$. (P) represents —P(R$^{10}$)$_3$$^+$X$^-$ or —PO(OR$^{11}$)$_2$ where R$^{10}$ represents aryl, preferably phenyl, or C$_1$–C$_4$-alkyl, preferably butyl, and R$^{11}$ represents alkyl, preferably methyl or ethyl, and X represents halogen, preferably chlorine, bromine or iodine.

The phosphorus compounds of the formula (VI) are known organic chemicals for synthesis.

The thioamides required as starting materials to carry out the process d) according to the invention are defined in a general way by the formula (VII). In this formula (VII), Ar, E, G and Z each preferably or in particular have those meanings already given in connection with the description of the compounds of the formula (I) according to the invention as preferred or as particularly preferred for Ar, E, G and Z.

Some of the thioamides of the formula (VII) are known and/or can be prepared by processes known per se (cf. for example EP-A 528 681).

The halogenoalkyl compounds or acetylene compounds further required as starting materials to carry out the process d) according to the invention are defined in a general way by the formulae (VIII) and (IX), respectively. In the formula (VIII), R$^{12}$ represents hydrogen or alkyl, preferably hydrogen or methyl. Y$^1$ represents cyano, alkylcarbonyl, arylcarbonyl, formyl, dialkoxyalkyl or alkoxycarbonyl, preferably cyano, formyl, diethoxymethyl, dimethoxymethyl, methoxycarbonyl, ethoxycarbonyl, benzoyl or acetyl. X$^1$ represents halogen, preferably chlorine or bromine. In the formula (IX), Y$^2$ represents alkoxycarbonyl, preferably methoxycarbonyl or ethoxycarbonyl. Y$^3$ represents hydrogen, alkyl, aryl, alkylcarbonyl, arylcarbonyl or alkoxycarbonyl, preferably hydrogen, methyl, ethyl, phenyl, acetyl, benzoyl, methoxycarbonyl or ethoxycarbonyl.

The halogenoalkyl compounds of the formula (VIII) are known chemicals for synthesis.

Suitable diluents for carrying out the processes a), b), c) and d) according to the invention are all inert organic solvents. These include preferably aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether.

The processes a), b) and d) according to the invention can also be carried out in mixtures of the abovementioned solvents with water, or in pure water.

The processes a) and b) according to the invention are, if appropriate, carried out in the presence of an acid or a base.

The processes c) and d) according to the invention are, if appropriate, carried out in the presence of a suitable acid acceptor.

Suitable acids for carrying out the process a) and b) according to the invention are all inorganic and organic and also all polymeric acids. These include, for example, hydrogen chloride, sulphuric acid, phosphoric acid, formic acid, acetic acid, trifluoroacetic acid, methanesulphonic acid, trifluoromethanesulphonic acid, toluenesulphonic acid, acid ion exchangers, acid clays and acid silica gel.

Suitable bases or acid acceptors for carrying out the processes a), b), c) and d) according to the invention are all conventional inorganic or organic bases. These include preferably alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the processes a) and b) according to the invention, the reaction temperatures may be varied over a relatively wide range. In general, temperatures between −20° C. and +200° C., preferably between 20° C. and 150° C., are employed.

When carrying out the process c) according to the invention, the reaction temperatures may also be varied over a relatively wide range. In general, temperatures between −50° C. and +100° C., preferably temperatures between −20° C. and +50° C., are employed.

When carrying out the process d) according to the invention, the temperatures may also be varied over a relatively wide range. In general, temperatures between 0° C. and 150° C., preferably temperatures between 0° C. and 110° C., are employed.

The process a) according to the invention for preparing the compounds of the formula (I) is carried out by employing generally 1 to 15 mol, preferably 1 to 8 mol, of amine of the formula (III) per mole of the ketone of the formula (II).

The process b) according to the invention for preparing the compounds of the formula (I) is carried out by employing generally 0.5 to 15 mol, preferably 0.5 to 2 mol, of the diamine of the formula (V) per mole of the nitrile of the formula (IV).

The process c) according to the invention for preparing the compounds of the formula (I) is carried out by employing generally 0.5 to 15 mol, preferably 0.8 to 5 mol, of the keto compound of the formula (II) per mole of phosphorus compounds of the formula (VI).

The process d) according to the invention for preparing the compounds of the formula (I) is carried out by employing generally 0.5 to 15 mol, preferably 0.8 to 5 mol, of the halogenoalkyl compound of the formula (VIII) or of the acetylene compound of the formula (IX) per mole of the thioamide of the formula (VII).

The processes a), b), c) and d) according to the invention are generally carried out at atmospheric pressure. However, it is also possible to work at elevated or reduced pressure—in general between 0.1 bar and 10 bar.

The reactions of the processes according to the invention are carried out and the reaction products of the processes according to the invention are worked up and isolated according to known methods (cf. also the Preparation Examples).

The active compounds according to the invention have a potent microbicidal activity and are employed in practice for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Some pathogens causing fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidial form: Drechslera, synonym: Helminthosporium);

Cochliobolus species, such as, for example, *Cochliobolus sativus* (conidiae form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Altemaria species, such as, for example, *Alternaria brassicae;*

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, for example against Erysiphe species, or diseases in viticulture, fruit-growing and horticulture, for example against Plasmopara species, or rice diseases, for example against Pyricularia species. The active compounds according to the invention are also employed very successfully for controlling other plant diseases, for example against Podosphaera species and Venturia species.

Depending on their particular physical and/or chemical properties, the active compounds can be converted, if desired, to the customary formulations, such as solutions, emulsions, suspensions, powders, foams, pastes, granules, aerosols and microencapsulations in polymeric substances and in coating compositions for seeds, and ULV cold and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water; liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide; suitable solid carriers are: for example, ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or, in their formulations, also as a mixture with known fingicides, bactericides, acaricides, nematicides or insecticides in order thus, for example, to widen the spectrum of action or to prevent development of resistance.

In many cases, synergistic effects are achieved.

Examples of co-components in mixtures are the following compounds:

Fungicides:
2-aminobutane; 2-anilino-4-methyl-6-cyclopropyl-pyrimidine; 2', 6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxy-phenyl)-acetamide; 8-hydroxyquinoline sulphate; methyl (E)-2-{2-[6-(2-cyanophenoxy)-pyrimidin- 4-yloxy]phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamrethrin, amitraz, avermectin, AZ 60541, azadirachtin, azinphos A, azinphos M, azocyclotin,

*Bacillus thuringiensis*, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157419, CGA 184699, chloethocarb, chlorethoxyfos, chlorfenvinphos, chlorfluazuron, chlonnephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb,
fenoxycarb, fenpropathrin, fenpyrad, fenpyroximate, fenthion, fenvalerate,
fipronil, fluazinam, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivemectin,
lamda-cyhalothrin, lufenuron,
malathion, mecarbam, mervinphos, mesulfenfos, metaldehyde, methacrifos,
methamidophos, methidathion, methiocarb, methomyl, metolcarb, milbemectin,
monocrotophos, moxidectin,
naled, NC 184, NI 25, nitenpyram,
omethoate, oxamyl, oxydemethon M, oxydeprofos,
parathion A, parathion M, permethrin, phenthoate, phorate, phosalone, phosmet,
phosphamdon, phoxim, pirimicarb, pirimiphos M, ,primiphos A, profenofos,
profenophos, promecarb, propaphos, propoxur, prothiofos, prothiophos, prothoate,
pymetrozin, pyrachlophos, pyraclofos, pyraclophos, pyradaphenthion, pyresmethrin, pyrethrum, pyridaben, pyrimidifen, pyriproxifen,
quinalphos,
RH 5992,
salithion, sebufos, silafluofen, sulfotep, sulprofos,
tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb,
vamidothion, XMC, xylylcarb, YI 5301/5302, zetamethrin.

It is also possible to mix the active compounds according to the invention with other known active compounds, such as herbicides, or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by wetting, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required.

PREPARATION EXAMPLES

Example I-1

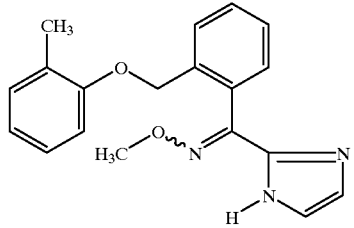

(Process a)

1 g (0.01197 mol) of methoxylamine hydrochloride and 2 g (0.00684 mol) of 2-[2-(2-methylphenoxymethyl)-benzoyl]-imidazole in 10 ml of ethylene glycol are heated to 150° C. for 1 hour. The reaction mixture is then admixed with a solution of 1.3 g of sodium carbonate in 25 ml of water. The mixture is extracted with ethyl acetate, and the organic phase is dried over sodium sulphate and concentrated under reduced pressure, on which the product crystallizes. 550 mg (25% of theory) of 2-{1-[2-(2-methylphenoxymethyl)-phenyl]-1-(methoximino)-methyl]-imidazole are obtained as a mixture of stereoisomers (E:Z= 82:18).

$^1$H NMR spectrum (CDCl$_3$/TMS): δ=2.146 (3H); 3.932 (3H); 4.977(2H); 6.724–6.841 (2H); 6.983–7.158 (4H); 7.293–7.322 (1H); 7.371–7.583 (2H); 7.583–7.630 (1H); 9.917 (1H) ppm.

The mother liquor is concentrated and the residue is chromatographed over silica gel using diethyl ether. The solvent is distilled off, leaving 520 mg (23.7% of theory) of isomerically pure Z-2-{1-[2-(2-methylphenoxymethyl)-phenyl]-1-(methoximino)-methyl}-imidazole.

$^1$H NMR spectrum (CDCl$_3$/TMS): δ=2.158 (3H); 4.115 (3H); 5.061 (2H); 6.697/- 6.725 (1H); 6.805/6.827 (1H); 7.027–7.3 (4H); 7.3–7.8 (4H); 11.0 (1H) ppm.

Preparation of the starting material

Example (II-1)

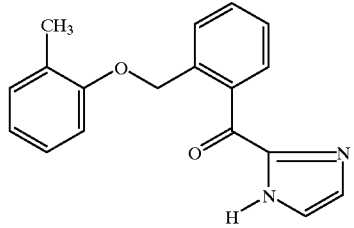

(Process a-a1)

At −40° C., 6.9 g (0.0405 mol) of N-diethoxymethylimidazole (J. Org. Chem. Vol. 45, No. 20, 1980, page 4040) in 40 ml of tetrahydrofuran are mixed with 11.3 g (0.0405 mol) of 23% pure n-butyllithium, and the mixture is stirred at −60° C. for one hour. At −40° C., 6 g (0.0203 mol) of N-[2-(2-methylphenoxymethyl)-benzoyl]-pyrrolidine are added, and the mixture is stirred for 30 minutes without any further cooling, on which the reaction mixture warms to 20° C. 5 g of ammonium chloride and 50 ml of methanol are added, and the mixture is heated at reflux for 15 minutes. The volatile components are distilled off under reduced pressure and the residue is admixed with water and extracted with ethyl acetate. The organic phase is dried and concentrated under reduced pressure. The residue is recrystallized from ethyl acetate. 3.79 g (63.8% of theory) of 2[2-(2-methylphenoxymethyl)-benzoyl]-imidazole are obtained.

$^1$H NMR spectrum (CDCl$_3$/TMS): δ=2.118 (3H); 5.357 (2H); 6.792–6.851 (2H); 7.059–7.2(3H); 7.343 (1H); 7.425/7.450/7.476 (1H); 7.537–7.592 (1H); 7.712/7.737 (1H); 8.200–8.230 (1H); 11.25 (1H) ppm.

Preparation of the precursor:

Example (Xa-1)

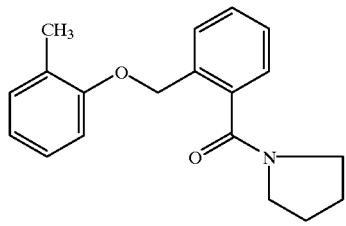

(Process a-a2)

At 20 to 30° C., 15.6 g (0.06 mol) of 2-(2-methylphenoxymethyl)benzoyl chloride (EP-A 493 711, page 22) are added dropwise to a solution of 8.53 g (0.12 mol) of pyrrolidine in 40 ml of t-butyl methyl ether. The mixture is admixed with water and the organic phase is separated off, dried over sodium sulphate and concentrated under reduced pressure. The residue crystallizes when stirred with diisopropyl ether. 15 g (84.6% of theory) of N-[2-(2-methylphenoxymethyl)-benzoyl]-pyrrolidine are obtained.

$^1$H NMR spectrum (CDCl$_3$/TMS): δ=1.746–1.952 (4H); 2.236 (3H); 3.205/3.227/3250 (2H); 3.597/3.621/3.643 (2H); 5.126 (2H); 6.842–6.925 (2H); 7.114–7.7.160 (2H); 7.257–7.441 (3H); 7.593–7,618 (1H) ppm.

Example (Xa-2)

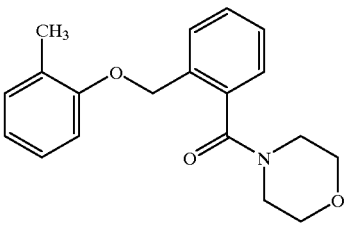

(Process a-a2)

At 20 to 30° C., 2.6 g (0.01 mol) of 2-(2-methylphenoxymethyl)benzoyl chloride (EP-A 493 711, page 22) are added dropwise to a solution of 1.8 g (0.02 mol) of morpholine in 40 ml of tert-butyl methyl ether. The mixture is admixed with water and the organic phase is separated off, dried over sodium sulphate and concentrated under reduced pressure. The residue is recrystallized from 5 ml of methanol. 1.6 g (51.4% of theory) of N-[2-(2-methylphenoxymethyl)-benzoyl]-morpholine are obtained.

$^1$H NMR spectrum (CDCl$_3$/TMS): δ=2.245 (3H); 3.32–3.42 (2H); 3.42–3.62 (2H); 3.62–3.85 (4H); 5.093 (2H); 6.866–6.916 (2H); 7.125–7.171 (2H); 7.235–7.264 (1H); 7.348–7.470 (2H); 7.599–7.624 (1H) ppm.

By the methods of Examples (Xa-1) and (Xa-2) and according to the general process description, the compounds of the formula (Xa) listed in Table 41 are prepared.

TABLE 41

| Ex. No. | $Z^4$ | $G^1$ | $R^{15}$ | $R^{16}$ | Physical data |
|---|---|---|---|---|---|
| Xa-3 | 2-methylphenyl | —O—CH$_2$— | —CH$_3$ | cyclohexyl | M$^+$ = 337 |
| Xa-4 | 2-methylphenyl | —O—CH$_2$— | —H | cyclohexyl | M$^+$ = 323 |
| Xa-5 | 2-methylphenyl | —O—CH$_2$— | —H | cyclopentyl | M$^+$ = 309 |

TABLE 41-continued
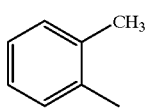
(Xa)
| Ex. No. | $Z^4$ | $G^1$ | $R^{15}$ | $R^{16}$ | Physical data |
|---|---|---|---|---|---|
| Xa-6 | 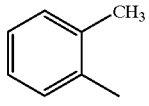 | —O—CH$_2$— | —H | —OCH$_3$ | M$^+$ = 271 |
| Xa-7 | 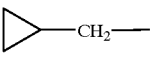 | —O—CH$_2$— | —H | 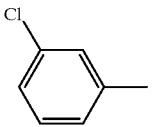 | M$^+$ = 295 |
| Xa-8 | 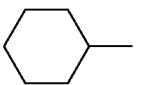 | —O—CH$_2$— | —CH$_3$ | 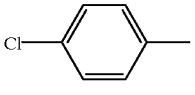 | M$^+$ = 358 |
| Xa-9 | 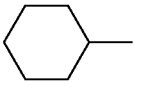 | —O—CH$_2$— | —CH$_3$ | 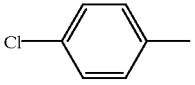 | M$^+$ = 358 |
| Xa-10 | 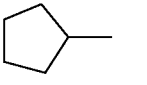 | —O—CH$_2$— | —H | 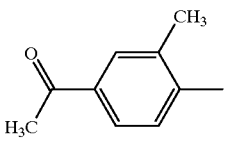 | M$^+$ = 330 |
| Xa-11 | 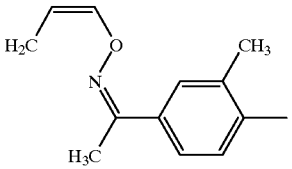 | —O—CH$_2$— | —H | —CH$_3$ | M$^+$ = 297 |
| Xa-12 | 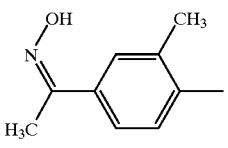 | —O—CH$_2$— | —H | —CH$_3$ | M$^+$ = 352 |
| Xa-13 |  | —O—CH$_2$— | —H | —CH$_3$ | M$^+$ = 312 |

TABLE 41-continued
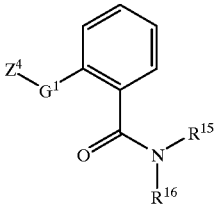
(Xa)
| Ex. No. | Z⁴ | G¹ | R¹⁵ | R¹⁶ | Physical data |
|---|---|---|---|---|---|
| Xa-14 | 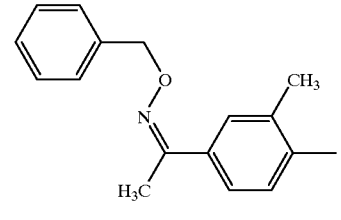 | —O—CH₂— | —H | —CH₃ | $M^+ = 402$ |
| Xa-15 | 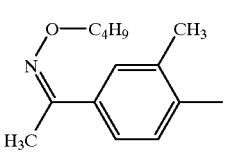 | —O—CH₂— | —H | —CH₃ | $M^+ = 354$ |
| Xa-16 | 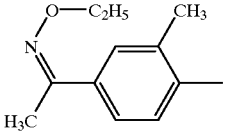 | —O—CH₂— | —H | —CH₃ | $M^+ = 368$ |
| Xa-17 | 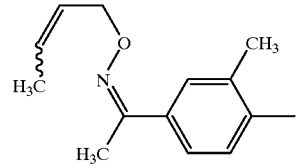 | —O—CH₂— | —H | —CH₃ | $M^+ = 340$ |
| Xa-18 | 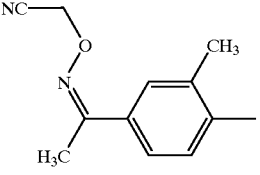 | —O—CH₂— | —H | —CH₃ | $M^+ = 366$ |
| Xa-19 |  | —O—CH₂— | —H | —CH₃ | $M^+ = 351$ |

TABLE 41-continued (Xa) structure: Z⁴-G¹ attached to benzene ring with C(=O)N(R¹⁵)(R¹⁶) group

| Ex. No. | Z⁴ | G¹ | R¹⁵ | R¹⁶ | Physical data |
|---|---|---|---|---|---|
| Xa-20 | 3-CF₃-C₆H₄-CH₂-O-N=C(CH₃)-(3,4-diMe-C₆H₃) | —O—CH₂— | —H | —CH₃ | $M^+ = 470$ |
| Xa-21 | 3-F-C₆H₄-CH₂-O-N=C(CH₃)-(3,4-diMe-C₆H₃) | —O—CH₂— | —H | —CH₃ | $M^+ = 434$ |
| Xa-22 | 2,4-diMe-C₆H₃- | —O—CH₂— | —H | —CH₃ | |
| Xa-23 | 2-Me-4-iPr-C₆H₃- | —O—CH₂— | —H | —CH₃ | $M^+ = 297$ |
| Xa-24 | 2-Et-C₆H₄- | —O—CH₂— | —H | —CH₃ | $M^+ = 269$ |
| Xa-25 | 2-Me-C₆H₄- | —O—CH₂— | —H | —C₂H₅ | $M^+ = 269$ |
| Xa-26 | 2,4-diMe-C₆H₃- | —O—CH₂— | —CH₃ | —CH₃ | $M^+ = 283$ |
| Xa-27 | 2-Me-4-iPr-C₆H₃- | —O—CH₂— | —CH₃ | —CH₃ | $M^+ = 311$ |

TABLE 41-continued (Xa)

| Ex. No. | Z⁴ | G¹ | R¹⁵ | R¹⁶ | Physical data |
|---|---|---|---|---|---|
| Xa-28 | 2-C₂H₅, 6-CH₃ phenyl | —O—CH₂— | —CH₃ | —CH₃ | M⁺ = 283 |
| Xa-29 | 2,4,5-tri CH₃ phenyl | —O—CH₂— | —H | —C₂H₅ | M⁺ = 283 |
| Xa-30 | 2-CH₃, 4-i-Pr phenyl (with extra CH₃) | —O—CH₂— | —H | —C₂H₅ | M⁺ = 311 |
| Xa-31 | 2-C₂H₅, 6-CH₃ phenyl | —O—CH₂— | —H | —C₂H₅ | M⁺ = 283 |
| Xa-32 | 3,4-di CH₃, acetyl phenyl | —O—CH₂— | —CH₃ | —CH₃ | |
| Xa-33 | 2,3-di CH₃ phenyl | —O—CH₂— | —H | —(CH₂)₂—OH | ¹H NMR: 2.24; 3.48–3.58; 3.59–3.68 |
| Xa-34 | 2,3-di CH₃ phenyl | —O—CH₂— | —H | —(CH₂)₃—OCH₃ | ¹H NMR: 2.268; 3.283 |
| Xa-35 | 2,3-di CH₃ phenyl | —O—CH₂— | —H | —CH₂CH₂CH(OH)CH₃ | ¹H NMR: 2.246; 1.128; 1.149 |
| Xa-36 | 2,3-di CH₃ phenyl | —O—CH₂— | —C₃H₇ | —C₃H₇ | ¹H NMR: 2.24; 3.1–3.3 |

TABLE 41-continued (Xa) structure: 2-substituted benzamide with Z⁴—G¹ at ortho position and C(=O)N(R¹⁵)(R¹⁶)

| Ex. No. | Z⁴ | G¹ | R¹⁵ | R¹⁶ | Physical data |
|---|---|---|---|---|---|
| Xa-37 | 2-methylphenyl | —O—CH₂— | —H | -2-C₇H₁₃ | ¹H NMR: 2.23; 1.07; 1.09 |
| Xa-38 | 2-methylphenyl | —O—CH₂— | —H | -Allyl | ¹H NMR: 2.23; 3.99–4.04 |
| Xa-39 | 2-methylphenyl | —O—CH₂— | —CH₃ | —CH₃ | ¹H NMR: 2.24; 2.842; 3.095 |
| Xa-40 | 2-methylphenyl | —O—CH₂— | —C₄H₉ | —C₄H₉ | ¹H NMR: 2.25; 3.0–3.1; 3.3–3.7 |
| Xa-41 | 2-methylphenyl | —O—CH₂— | —H | —CH₂CH(OH)CH₃ | ¹H NMR: 2.24; 1.16; 1.18 |
| Xa-42 | 2-methylphenyl | —O—CH₂— | —H | —(CH₂)₃—OH | ¹H NMR: 2.24; 1.61–1.69 |
| Xa-43 | 2-methylphenyl | —O—CH₂— | —H | 4-methylcyclohexyl | ¹H NMR: 2.23; 0.85; 0.87 |
| Xa-44 | 2-methylphenyl | —O—CH₂— | —H | —CH₃ | ¹H NMR: 2.24; 2.95; 2.965 |
| Xa-45 | 2,4-dimethylphenyl | —O—CH₂— | —H | —CH₃ | ¹H NMR: 2.201; 2.328; 2.946; 2.962 |
| Xa-46 | 2,4-dimethylphenyl | —O—CH₂— | —H | —C₂H₅ | ¹H NMR: 2.191; 2.332; 3.332–3.479 |

TABLE 41-continued (Xa)

| Ex. No. | Z⁴ | G¹ | R¹⁵ | R¹⁶ | Physical data |
|---|---|---|---|---|---|
| Xa-47 | 2,4,5-trimethylphenyl with C(=O)CH₃ | —O—CH₂— | —H | —CH₃ | ¹H NMR: 2.17; 2.44; 2.72; 2.74 |
| Xa-48 | 2,4-dimethylphenyl | —O—CH₂— | —H | —C₃H₇ | ¹H NMR: 2.192; 2.328; 3.322–3.389 |
| Xa-49 | 2,4-dimethylphenyl | —O—CH₂— | —H | —(CH₂)₂—OH | ¹H NMR: 2.19; 2.33; 3.52–3.57; 3.68–3.72 |
| Xa-50 | 2,4-dimethylphenyl | —O—CH₂— | —H | —(CH₂)₃—CH(OH)—CH₃ | ¹H NMR: 2.22; 2.32; 3.29 |
| Xa-51 | 2,4-dimethylphenyl | —O—CH₂— | —C₃H₇ | —C₃H₇ | ¹H NMR: 2.21; 2.30; 3.05–3.10; 3.46–3.71 |
| Xa-52 | 2,4-dimethylphenyl | —O—CH₂— | —H | —OCH₃ | m.p.: 106° C. |

Example (I-3)

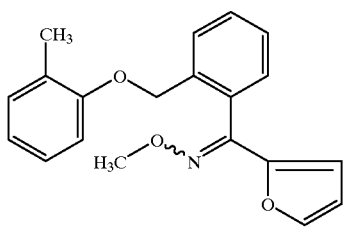

(Process a)

1.67 g (0.02 mol) of O-methylhydroxylammonium chloride in 10 ml of ethylene glycol are heated with 2.76 g (0.01 mol) of 2-[2-(2-methylphenoxymethyl)-benzoyl]-furan to 140° C. for one hour. The mixture is poured into water, the product is extracted with ethyl acetate and the organic phase is dried over sodium sulphate and concentrated under reduced pressure. The residue is chromatographed over silica gel using tert-butyl methyl ether/petroleum ether (1:1).

1 g (31.2% of theory) of 2-{1-[2-(2-methylphenoxymethyl)-phenyl]-1-(methoximino)-methyl}-furan is obtained as a mixture of stereoisomers (E:Z=44:52 (HPLC)).

¹H NMR spectrum (CDCl₃/TMS): δ=2.192–2.205; 3.978; 4.087; 5.012; 6.1–7.8 ppm

GC/MS analysis:

E-isomer: retention index=2285, M=322, 321, 290, 214, 199, 183, 154, 127, 89, 77, 39.

Z-isomer: retention index=2320, M=321, 290, 246, 214, 199, 183, 154, 127, 89, 77, 39.

Preparation of the starting material:

Example (II-2)

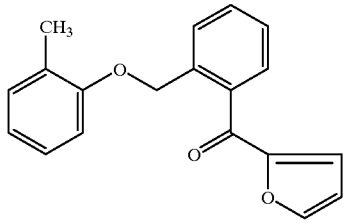

(Process a-a1)

27.8 g (0.1 mol) of 23% pure n-butyllithium are added dropwise within 15 minutes to a solution of 6.8 g (0.1 mol) of furan in 100 ml of diethyl ether which had been cooled to −20° C. The mixture was stirred at 20° C. for 2 hours, cooled once more to −20° C., and 14.8 g (0.05 mol) of N-[2-(2-methylphenoxymethyl)-benzoyl]-pyrrolidine dissolved in 100 ml of diethyl ether are added dropwise within 15 minutes. After complete conversion (DC control), the mixture is poured into 300 ml of ice-cold ammonium chloride solution and extracted with ethyl acetate. The organic phase is dried over sodium sulphate and concentrated under reduced pressure. 13.1 g (89.7% of theory) of 2-[2-(2-methylphenoxymethyl)-benzoyl]-furan are obtained.

$^1$H NMR spectrum (CDCl$_3$/TMS): δ=2.129 (3H); 5.266 (2H); 6.536–6.554 (1H); 6.803–6.849 (2H); 7.0–7.763 (8H) ppm.

Example (I-4)

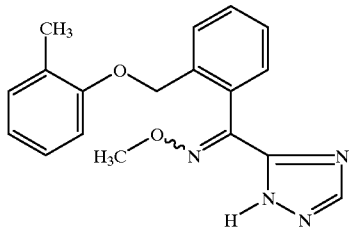

(Process a)

1.45 g (0.005 mol) of 3-[2-(2-methylphenoxymethyl)-benzoyl]-triazole and 1.25 g (0.015 mol) of O-methylhydroxylammonium chloride in 5 ml of ethylene glycol are heated to 180° C. for 2 hours. The mixture is admixed with aqueous sodium bicarbonate solution and extracted with ethyl acetate and the organic phase is dried over sodium sulphate and concentrated under reduced pressure. The residue is chromatographed over silica gel using diethyl ether/petroleum ether (3:1). 0.7 g (43% of theory) of 3-{1-[2-(2-methylphenoxymethyl)-phenyl]-1-(methoximino)-methyl}-triazole is obtained as a mixture of stereoisomers (E:Z=59:24 (HPLC)).

$^1$H NMR spectrum (CDCl$_3$/TMS): δ2.077; 2.112; 4.010; 4.167; 4.974; 5.072; 6.6–8.1 ppm.

Preparation of the starting material

(Example II-3)

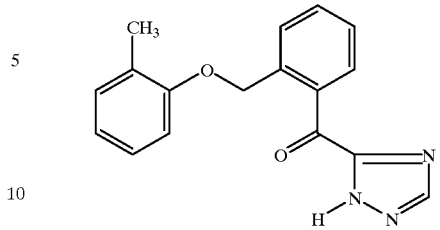

(Process a-a1)

At −20° C., 2.8 g (0.01 mol) of 23% pure n-butyllithium are added dropwise within 15 minutes to a solution of 1.7 g (0.01 mol) of N-diethoxymethyltriazole in 10 ml of tetrahydrofuran. Stirring is continued for 15 minutes at −20° C., and 1.48 g (0.005 mol) of N-[2-(2-methylphenoxymethyl)-benzoyl]-pyrrolidine dissolved in 10 ml of tetrahydrofuran are then added, and the mixture is stirred for a further 30 minutes at −20° C. 2 g of ammonium chloride and 10 ml of methanol are added and the mixture is heated under reflux for 15 minutes. The volatile components are removed under reduced pressure, the residue is admixed with water and extracted with ethyl acetate, and the organic phase is dried over sodium sulphate and concentrated under reduced pressure. The residue crystallizes when treated with a mixture of diethyl ether and petroleum ether in the ratio of 1:1. 0.5 g (17% of theory) of 3-[2-(2-methylphenoxymethyl)-benzoyl]-triazole of melting point 179° C. is obtained.

$^1$H NMR spectrum (CDCl$_3$/TMS): δ=1.884 (3H); 5.224 (2H); 6.769–6.866 (2H); 7.047–7.104 (2H); 7.379–7.505 (1H); 7.502–7.688 (2H); 7.688–7.85 (1H); 8.652 (1H); 14.742 (1H) ppm.

Preparation of the precursor (using the method of the N-diethoxymethylimidazole preparation of J. Org. Chem. Vol. 45, No. 20, 1980, page 4040):

After the addition of 2.5 g of p-toluenesulphonic acid hydrate, 34.5 g (0.5 mol) of triazole in 222 g (1.5 mol) of triethyl orthoforrnate are heated until the internal temperature reaches 150° C., while ethanol is distilled off. 2 g of sodium carbonate are added and the mixture is distilled using high vacuum. 48.6 g (56.8% of theory) of N-diethoxymethyltriazole are obtained.

$^1$H NMR spectrum (CDCl$_3$/TMS): δ=1.247/1.270/1.294 (6H); 3.647/3.671/3.694/3.718 (4H); 6.262 (1H); 7.994 (1H); 8.443 (1H) ppm.

Example (I-5)

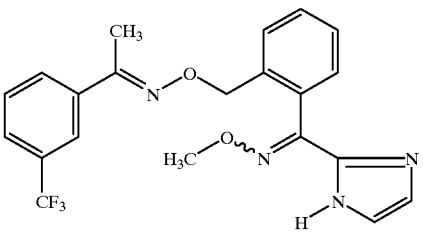

(Process b)

5.6 g (0.015 mol) of 2-(methoximino)-2-{2-[1-(3-trifluoromethylphenyl)-ethylidene-aminooxymethyl]-phenyl}-acetonitrile (cf. WO-A 94/26700) and 1.6 g (0.015 mol) of aminoacetaldehyde dimethylacetal are heated under reflux for 2 hours. The mixture is admixed with aqueous hydrochloric acid, neutralized with aqueous sodium carbonate solution and extracted with ethyl acetate, and the organic phase is dried over sodium sulphate and concentrated under reduced pressure. The residue is chromatographed over silica gel using tert-butyl methyl ether/petroleum ether (3:1). 2- {1 -(Methoximino)- 1 -[2-<3-trilfluoromethylphenyl>-ethylidene-aminooxymethyl)-phenyl]-methyl}-imidazole is obtained.

Example (I-6)

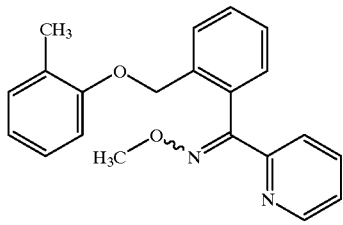

(Process a)

1.07 g (0.0198 mol) of sodium methoxide and then 3 g (0.00988 mol) of 2-[2-(2-methylphenoxymethyl)-benzoyl]-pyridine are added to 1.65 g (0.0198 mol) of O-methylhydroxylammonium chloride in 10 ml of methanol. The mixture is heated under reflux for 2 hours. An additional 0.82 g of O-methylhydroxylanmmonium chloride and 0.53 g of sodium methoxide are added, and the mixture is heated under reflux for a further 2 hours. The mixture is poured into water, extracted with diethyl ether, dried over sodium sulphate and concentrated under reduced pressure. 2.3 g (69.9% of theory) of a mixture of 2-{1-[2-(2-methylphenoxymethyl)-phenyl]-1-(methoximino)-methyl}-pyridine stereoisomers (E:Z=75:25 (GC/MS)) is obtained.

$^1$H NMR spectrum (CDCl$_3$/TMS): δ=2.172 (3H, E); 2.246 (3H, Z); 3.999 (3H, Z); 4.040 (3H, E); 4.956 (2H, E); 5.008 (2H, Z); 6.6–6.9 (2H, E+Z); 7.0–7.15 (2H, E+Z); 7.125–7.3 (2H, E+Z); 7.38–7.5 (2H, E+Z); 7.55–7.75 (3H, E+Z); 8.6–8.7 (1H, E+Z) ppm.
GC/MS analysis:
E isomer: retention index=2463
M=333, 332, 301, 186, 241, 225, 193, 168, 152, 116, 89, 78, 51.
Z isomer: retention index=2509
M=303, 301, 283, 257, 225, 193, 168, 152, 116, 89, 78, 51.
Preparation of the starting material Example (II-4)

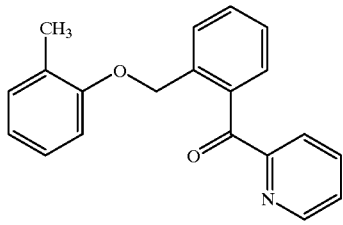

(Process a-c1)

10 g (0.036 mol) of 2-[(2-methylphenoxy)-methyl]-1-bromo-benzene (EP-A 525 516, page 113) are dissolved in 40 ml of tetrahydrofuran. 3 g of this solution are added to 0.88 g (0.036 mol) of magnesium turnings. After the addition of a drop of bromine, the mixture is heated. Once the reaction has set in, the remainder of the bromine compound dissolved in tetrahydrofuran is added and the mixture is heated under reflux for one hour. At −20° C., 3.76 g (0.036 mol) of 2-cyanopyridine dissolved in 10 ml of tetrahydrofuran are then added to the reaction mixture, and the mixture is stirred at −20° C. for 1 hour. A solution of 10 g of ammonium chloride in 100 ml of water is added and the crude intermediate (the ketimine of the end product) is extracted with diethyl ether. The solution is concentrated and the residue is admixed with a mixture of 15 ml of 36% strength aqueous hydrochloric acid, 50 ml of water and 100 ml of dimethylformamide. The mixture is stirred at 25° C. for one hour and ice is then added to the mixture which is made alkaline with 50% strength aqueous sodium hydroxide solution and extracted with diethyl ether. The organic phase is dried over sodium sulphate and concentrated under reduced pressure. The residue is chromatographed over silica gel using diethyl ether/petroleum ether (1:1). 3.94 g (36% of theory) of 2-[2-(2-methylphenoxymethyl)-benzoyl]-pyridine are obtained.

$^1$H NMR spectrum (CDCl$_3$/TMS): δ=2.127 (3H); 5.211 (2H); 6.698/6.725 (1H); 6.777–6.829 (1H); 7.015–7.088 (2H); 7.397–7.442 (2H); 7.528–7.638 (2H); 7.683/7.685 (1H); 7.709–7.835 (1H); 8.019–8.052 (1H); 8.656–8.680 (1H) ppm.
GC/MS analysis:
Retention index=2479
M=305, 303, 285, 257, 225, 196, 167, 139, 115, 89, 78, 51.

Example (I-7)

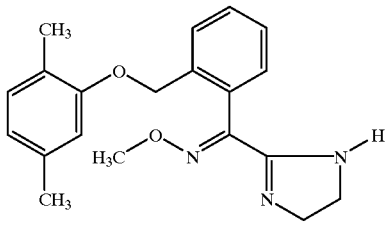

(Process b)

1 g (0.0034 mol) of 2-methoximino-2-[2-(2,4-dimethylphenoxymethyl)-phenyl]-acetonitrile is admixed with 0.2 g (0.0332 mol) of ethylenediamine and heated to 100° C. for 1 hour, until the formation of gas ceases. Recrystallization from a little ethanol affords 0.65 g (56.7% of theory) of 2-{1-methoximino-[2-(2,4-dimethyl-phenoxymethyl)-phenyl]-methyl}-4,5-dihydro-1H-imidazole.

$^1$H NMR spectrum (CDCl$_3$/TMS): δ=2.212 (3H); 2.276 (3H); 3.682 (4H); 3.947 (3H); 4.956 (2H); 6.616–6.669 (2H); 6.996–7.020 (1H); 7.210–7.243 (1H); 7.337–7.425 (2H); 7.556/7.579 (1H) ppm.
Preparation of the starting material:

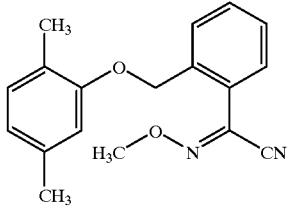

3.2 g (0.0404 mol) of pyridine and 6.2 g (0.0198 mol) of 2-methoximino-2-[2-(2,4-dimethylphenoxymethyl)- phenyl]-acetamide (Example No. 2 from EP-A 596 692) are charged initially in 50 ml of dichloromethane. With cooling, 4.6 g (0.0219 mol) of trifluoroacetic anhydride are added, and the mixture is left standing at room temperature for one hour. The mixture is washed with water and sodium bicarbonate solution. The solvent is removed under reduced pressure, affording 5.7 g (97.6% of theory) of 2-methoximino-2-[2-(2,4-dimethylphenoxymethyl)-phenyl]-acetonitrile.

$^1$H NMR spectrum (CDCl$_3$/TMS): δ=2.230 (3H); 2.311 (3H); 4.036 (3H); 5.011 (2H); 6.628 (1H); 6.687/6.712 (1H); 7.021/7.046 (1H); 7.361–7.529 (3H); 7.594/7.596 (1H) ppm.

Example (I-8)

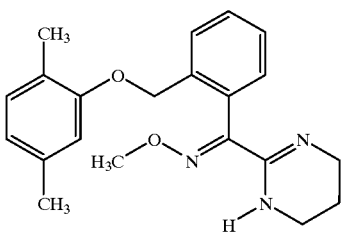

(Process b)

1 g (0.0034 mol) of 2-methoximino-2-[2-(2,4-dimethylphenoxymethyl)-phenyl]-acetonitrile is admixed with 250 mg (0.00337 mol) of 1,3-diaminopropane and heated to 100° C. for 1 hour. Recrystallization from 5 ml of ethanol affords 630 mg of 2-{1-methoximino-1-[2-(2,4-dimethylphenoxymethyl)-phenyl]-methyl}-1,4,5,6-tetrahydro-pyrimidine of melting point 144–145° C.

$^1$H NMR spectrum (CDCl$_3$/TMS): δ=1.716–1.793 (2H); 2.225 (3H); 2.278 (3H); 3.39–3,417 (4H); 3.905 (3H); 4.958 (2H); 6.629–6.669 (2H); 7.0–7.025 (1H); 7.158–7.187 (1H); 7.305–7.399 (2H); 7.518–7.547 (1H) ppm.

Example (I-9)

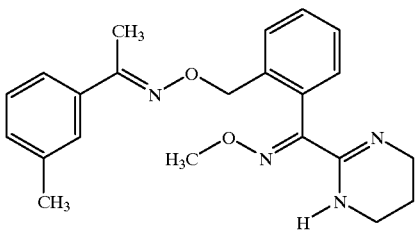

(Process b)

5.6 g (0.015 mol) of 2-(methoximino)-2-{2-[1-(3-trifluoromethylphenyl)-ethylidene-aminooxymethyl]-phenyl}-acetonitrile (cf. WO-A 94/26700) and 1.11 g (0.015 mol) of 1,3-diaminopropane are heated to 100° C. for 1 hour. 2-{1-(Methoximino-1-{2-[1-(3-trifluoromethylphenyl)-ethylidene-aminooxymethyl]-phenyl}-methyl}-1,4,5,6-tetrahydropyrimidine is obtained.

GC/MS analysis:
Retention index=2672
M=431, 401, 393, 246, 216, 198, 186, 145, 116, 84, 55, 30.

Example (I-10)

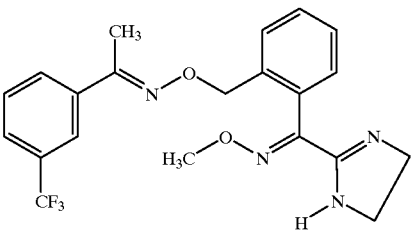

(Process b)

5.6 g (0.015 mol) of 2-(methoximino)-2-{2-[1-(3-trifluoromethylphenyl)-ethylidene-aminooxymethyl]-phenyl}-acetonitrile (cf. WO-A 94/26700) and 0.9 g (0.015 mol) of ethylenediamine are heated to 100° C. for 2 hours. Chromatography using petroleum ether/tert-butyl methyl ether (1:1) affords 3.5 g (55.7% of theory) of 2-{1-(methoximino)-1-{2-[1-(3-trifluoromethylphenyl)-ethylidene-aminooxymethyl]-phenyl}-methyl}-4,5-dihydro-1H-imidazole.

GC/MS analysis:

Retention index=2595
M=419, 379, 359, 232, 201, 184,145, 116, 89, 70, 44.
$^1$H NMR spectrum (CDCl$_3$/TMS):
δ=2.235 (3H); 3.3–3.9 (4H); 3.936 (3H); 7.1–8.0 (8H) ppm.

Example (I-11)

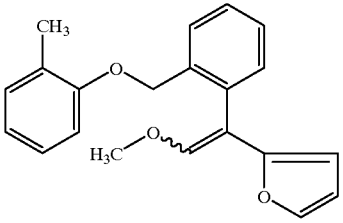

(Process c)

13.7 g (0.04 mol) of methoxymethyltriphenylphosphonium chloride in 40 ml of tetrahydrofuran are stirred at 20° C. with 4.5 g (0.04 mol) of potassium tert-butoxide for 30 minutes. 2.9 g (0.01 mol) of 2-[2-(2-methylphenoxymethyl)-benzoyl]-furan are then added, the mixture is heated under reflux for 2 hours, water and ethyl acetate are added, the organic phase is concentrated and the residue is chromatographed over silica gel using petroleum ether/diethyl ether (3:1). 1.4 g (43.7% of theory) of 2-{1-[2-(2-methylphenoxymethyl-phenyl]-2-(methoxy)-ethenyl}-furan are obtained as a mixture of stereoisomers (E:Z=70:30).

$^1$H NMR spectrun (CDCl$_3$/TMS), E isomer: δ=2.264 (3H); 3.715 (3H); 5.046 (2H); 5.681/5.692 (1H); 6.273–6.290 (1H); 6.6–7.8 (9H) ppm.

Example (I-12)

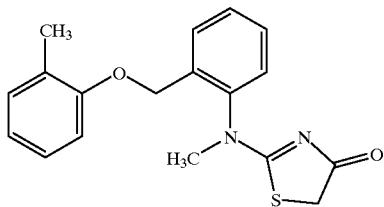

(Process b)

A solution of 6.3 g (0.01 mol) of 40% pure N-[2-(2-methylphenoxymethyl)-phenyl]-N-methyl-cyanamide, 1.1 g (0.01 mol) of methyl thioglycolate and 0.15 g of triethylamine in 100 ml of ethanol is heated under reflux for 18 hours. The mixture is concentrated and the residue is chromatographed over silica gel using cyclohexane/ethyl acetate (1:3). 1.4 g (43% of theory) of 2-{methyl-[2-(2-methylphenoxymethyl)-phenyl]-amino}-thiazol-4-one are obtained.

$^1$H NMR spectrum (CDCl$_3$/TMS): δ=2.26 (s, 3H); 3.62 (s, 3H); 3.90 (s, 3H); 5.015 (q, 2H).

By the same method, 2-{methyl-[2-(2-methylphenoxymethyl)-phenyl]-amino}-thiazol-4-one, Example (I-13) of melting point 155° C. is obtained.

Preparation of the starting material for Example I-12

Example (IVa-1)

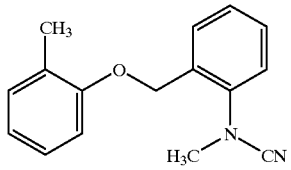

1 g (0.024 mol) of a 60% sodium hydride suspension is suspended in 10 ml of dimethylformamide and admixed with a solution of 2.2 g (0.02 mol) of ortho-cresol in 10 ml of dimethylformamide, and the mixture is stirred at 20° C. for 40 minutes. A solution of 11.3 g (0.02 mol) of 40% pure N-(2-bromomethylphenyl)-N-methyl-cyanamide in 10 ml of dimethylformamide is added, and the mixture is stirred at 20° C. for 18 hours. The mixture is stirred into 200 ml of ice/sodium chloride solution and extracted with ether. The combined organic phases are dried over Na$_2$SO$_4$ and concentrated under reduced pressure. The residue is chromatographed over silica gel using cyclohexane/ethyl acetate (3:1). 6.3 g of N-[2-(2-methylphenoxymethyl)-phenyl]-N-methyl-cyanamide of a content of 40% (HPLC) are obtained.

$^1$H NMR (CDCl$_3$/TMS): δ=2.41 (s, 3H); 5.20 (s, 2H) ppm.

By the same method, N-[2-(2,4-dimethylphenoxymethyl)-phenyl]-N-methyl-cyanamide Example (IVa-2) (starting material for Example I-13) is obtained.

$^1$H NMR (CDCl$_3$/TMS): δ=2.22 (s, 3H); 2.38 (s, 3H); 5.16 (s, 2H) ppm.

Preparation of the precursor:

Example (XXII-1)

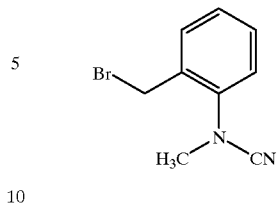

22.6 g (0.155 mol) of N-(2-methylphenyl)-N-methyl-cyanamide are dissolved in 300 ml of carbon tetrachloride, admixed with about 5 g of N-bromosuccinimide and 0.1 g of azodiisobutyronitrile and radiated using a UV lamp (250 W) for 5 hours with stirring. Over this period, more N-bromosuccinimide (a total of 32.9 g (0.185 mol)) is added a little at a time. The temperature increases during the reaction, until the solution boils at reflux. The reaction mixture is cooled and filtered, and the filtrate is concentrated under reduced pressure. 30 g of N-(2-bromomethyl-phenyl)-N-methyl-cyanamide of a content of 40% (HPLC) are obtained.

$^1$H NMR (CDCl$_3$/TMS): δ=3.37 (s, 3H); 4.66 (s, 2H) ppm.

Example (I-14)

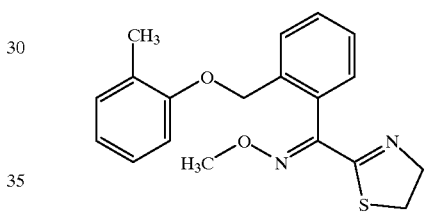

(Process d)

A solution of 1.6 g (0.0051 mol) of 2-methoximino-2-[2-(2-methylphenoxymethyl)-phenyl]-thioacetamide and 1.5 g (0.0076 mol) of bromoacetaldehyde diethyl acetal in 50 ml of ethanol is heated under reflux. After 18 hours, a further gram of bromoacetaldehyde diethyl acetal and 1 ml of glacial acetic acid are added, and the mixture is heated under reflux for a further 5 hours. The mixture is concentrated and the residue is taken up in dichloromethane and washed first with sodium bicarbonate solution and then with water. The organic phase is separated off, dried over sodium sulphate and concentrated. The residue is chromatographed over 100 g of silica gel using cyclohexane/ethyl acetate (3:1). 1.01 g (59% of theory) of 2-{methoximino-[2-(2-methylphenoxymethyl)-phenyl]-methyl}-thiazole are obtained.

$^1$H NMR (CDCl$_3$/TMS): δ=2.16 (s, 3H); 4.01 (s, 3H); 4.98 (s, 2H) ppm.

By the method of Example (I-14) and according to the general description of process d)

Example (I-15)

4,5-dihydro-2-{methoximino-[2-(2-methylphenoxymethyl)-phenyl]-methyl}-thiazole of melting point 82° C.,

Example (I-16)

4-ethoxy-2-{methoximino-[2-(2-methylphenoxymethyl)-phenyl]-methyl}-thiazole of melting point 65° C.,

Example (I-17)

4-ethoxy-5-methyl-2-{methoximino-[2-(2-methylphenoxymethyl)-phenyl]-methyl}-thiazole of melting point 71° C.,

Example (I-18)

4-methyl-2-{methoximino-[2-(2-methylphenoxymethyl)-phenyl]-methyl}-thiazole of melting point 99° C. and

Example (I-19)

5-ethoxycarbonylmethylidene-4-oxo-2-{methoximino-[2-(2-methyl-phenoxymethyl)-phenyl]-methyl}-thiazole; $^1$H NMR (CDCl$_3$/TMS): δ=2.24; 2.25; 3.82; 3.86; 6.53; 6.58 ppm are obtained.

Example A

Plasmopara test (vines)/protective

Solvent: 4.7 parts by weight of acetone
Emsulsifier: 0.3 part by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous spore suspension of Plasmopara viticola and then remain in a humidity chamber at 20 to 22° C. and 100% relative atmospheric humidity for 1 day. The plants are then placed in a greenhouse at 21° C. and about 90% atmospheric humidity for 5 days. The plants are then moistened and placed in a humidity chamber for 1 day.

Evaluation is carried out 6 days after the inoculation.

In this test, for example, the following compounds (I-7) and (I-8) exhibit an efficacy of 71 to 88% at an active compound concentration of 100 ppm.

TABLE A

Plasmopara test (vines)/protective

| Active compound | Efficacy in % of the untreated control at an active compound concentration of 100 ppm |
|---|---|
| (according to the invention) (I-7) | 88 |
| (according to the invention) (I-8) | 71 |

Example B

Erysiphe test (barley)/protective

Solvent: 10 parts by weight of N-methyl-pyrrolidone
Emulsifier: 0.6 part by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of *Erysiphe graminis f sp.hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, for example, the following compound (I-6) exhibit an efficacy of 88% at an active compound application rate of 125 g/ha.

TABLE B

Erysiphe test (barley)/protective

| Active compound | Efficacy in % of the untreated control at an active compound application rate of 125 g/ha |
|---|---|
| (according to the invention) (I-6) | 88 |

Example C
Pyricularia test (rice)/protective
  Solvent: 12.5 parts by weight of acetone
  Emsulsifier: 0.3 part by weight of alkylaryl polyglycol ether
  To produce a suitable preparation of active compound, 1 part by weight of active compound is mixed with the stated amounts of solvent, and the concentrate is diluted with water and the stated amount of emulsifier to the desired concentration.
  To test for protective activity, young rice plants are sprayed with the preparation of active compound until dripping wet. 4 days after the spray coating has dried on, the plants are inoculated with an aqueous spore suspension of *Pyricularia oryzae*. The plants are then placed in a greenhouse at 100% relative atmospheric humidity and 25° C.
  Evaluation of the disease infestation is carried out 4 days after the inoculation.
  In this test, for example, the following compound (I-3) exhibits an efficacy of 100% at an active compound concentration of 0.05%.

TABLE C

Pyricularia test (rice)/protective

| Active compound | Active compound concentration in % | Efficacy in % of the untreated control |
|---|---|---|
| 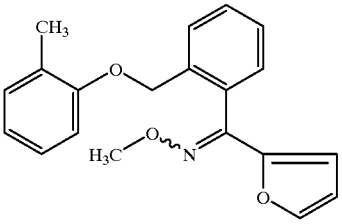 (according to the invention) (I-3) | | |

What is claimed is:
1. A compound of the formula (I):

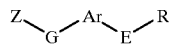 (I)

in which
  Ar represents phenylene or naphthylene, each of which is optionally substituted by a substituent selected from the group consisting of:
  a) halogen;
  b) cyano;
  c) nitro;
  d) amino;
  e) hydroxyl;
  f) formyl;
  g) carboxyl;
  h) carbamoyl;
  i) thiocarbamoyl;
  j) straight-chain or branched alkyl, alkoxy, alkylthio, alkylsulfinyl or alkylsulfonyl, each of which has 1 to 6 carbon atoms;
  k) straight-chain or branched alkenyl, alkenyloxy or alkynyloxy, each of which has 2 to 6 carbon atoms;
  l) straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms;
  m) straight-chain or branched halogenoalkenyl or halogenoalkenyloxy, each of which has 2 to 6 carbon atoms and 1 to 13 identical or different halogen atoms;
  n) straight-chain or branched alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in each alkyl moiety; and
  o) alkylene or dioxyalkylene, each of which has 1 to 6 carbon atoms, is attached to said phenylene or naphthylene twice, and is optionally mono- or polysubstituted independently by halogen, straight-chain or branched alkyl having 1 to 4 carbon atoms and straight-chain or branched halogenoalkyl having 1 to 4 carbon atoms and 1 to 9 identical or different halogen atoms;
E represents a 2-aza-1-alkene-1,1-diyl group which contains a radical $R^2$ in position 2;
$R^2$ represents hydrogen, amino, hydroxyl or cyano, or represents alkyl, alkoxy, alkylamino or dialkylamino, each of which has 1 to 6 carbon atoms in each alkyl moiety and is optionally substituted by halogen, cyano or $C_{1-4}$-alkoxy;
G represents —$CH_2$—Q— or —Q—$CH_2$—;
Q represents oxygen;
R represents furyl which is attached to E via a carbon atom and which is optionally substituted by alkyl, alkoxy or hydroxy; and
Z represents phenyl or naphthyl, each of which is optionally substituted by a substituent selected from the group consisting of:
  a) halogen;
  b) cyano;
  c) nitro;
  d) amino;
  e) hydroxyl;
  f) formyl;
  g) carboxyl;
  h) carbamoyl;
  i) thiocarbamoyl;
  j) straight-chain or branched alkyl, alkoxy, alkylthio, alkylsulfinyl or alkylsulfonyl, each of which has 1 to 6 carbon atoms;
  k) straight-chain or branched alkenyl or alkenyloxy, each of which has 2 to 6 carbon atoms;
  l) straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms;
  m) straight-chain or branched halogenoalkenyl or halogenoalkenyloxy, each of which has 2 to 6 carbon atoms and 1 to 13 identical or different halogen atoms;
  n) straight-chain or branched alkylamino, dialkylamino, alkylcarbonyl, alkylcarbonyloxy, alkoxycarbonyl or alkylsulfonyloxy, each of which has 1 to 6 carbon atoms in each alkyl moiety;
  o) alkylene or dioxyalkylene, each of which has 1 to 6 carbon atoms, is attached to said phenyl or naphthyl twice, and is optionally mono- or polysubstituted independently by halogen, straight-chain or branched alkyl having 1 to 4 carbon atoms and straight-chain or branched halogenoalkyl having 1 to 4 carbon atoms and 1 to 9 identical or different halogen atoms;

p) cycloalkyl having 3 to 6 carbon-atoms;
q) a grouping of the formula:

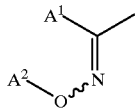

in which

A$^1$ represents alkyl having 1 to 4 carbon atoms or cycloalkyl having 1 to 6 carbon atoms; and A$^2$ represents alkyl having 1 to 4 carbon atoms, or alkenyl or alkynyl each having 2 to 4 carbon atoms, wherein said alkyl, alkenyl or alkynyl are optionally substituted by cyano, C$_{1-4}$-alkoxy, C$_{1-4}$-alkylthio, C$_{1-4}$-alkylamino, C$_{1-2}$-dialkylamino, phenyl, halogenophenyl, methylphenyl, trifluoromethylphenyl or C$_{1-2}$-alkoxyphenyl.

2. A compound of the formula:

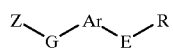 (I)

in which

Ar represents ortho-, meta- or para-phenylene, each of which is optionally substituted by a substituent selected from the group consisting of:
a) fluorine;
b) chlorine;
c) cyano;
d) methyl;
e) ethyl;
f) trifluoromethyl;
g) methoxy;
h) ethoxy;
i) methylthio;
j) methylsulfinyl; and
k) methylsulfonyl;

E represents a group of the formula:

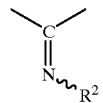

R$^2$ represents hydrogen, amino, hydroxyl or cyano, or represents methyl, ethyl, methoxy, ethoxy, methylamino, ethylamino or dimethylamino, each of which is optionally substituted by fluorine, chlorine, cyano, methoxy or ethoxy;

G represents —CH$_2$—Q— or —Q—CH$_2$—;
Q represents oxygen;

R represents furyl which is attached to E via a carbon atom and which is optionally substituted by methyl, methoxy or hydroxy; and Z represents phenyl or naphthyl, each of which is optionally substituted one to three times by substituents independently selected from the group consisting of:
a) fluorine, chlorine or bromine;
b) cyano;
c) nitro;
d) amino;
e) hydroxyl;
f) formyl;
g) carboxyl;
h) carbamoyl;
i) thiocarbamoyl;
j) methyl, ethyl, n-propyl, i-propyl, n-butyl, i-butyl, s-butyl, t-butyl, methoxy, ethoxy, n-propoxy, i-propoxy, methylthio, ethylthio, n-propylthio, i-propylthio, methylsulfinyl, ethylsulfinyl, methylsulfonyl or ethylsulfonyl;
k) trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulfinyl or trifluoromethylsulfonyl;
l) methylamino, ethylamino, n-propylamino, i-propylamino, dimethylamino, diethylamino, acetyl, propionyl, acetyloxy, methoxycarbonyl, ethoxycarbonyl, methylsulfonyloxy or ethylsulfonyloxy;
m) propane-1,3-diyl, methylenedioxy or ethylenedioxy, each of which is attached to said phenyl or naphthyl twice, and is optionally mono- or polysubstituted independently by fluorine, chlorine, methyl, trifluoromethyl, ethyl, n-propyl or i-propyl;
n) cyclopropyl, cyclobutyl, cyclopentyl or cyclohexyl; and
o) a grouping of the formula:

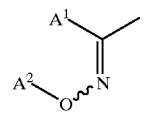

in which

A$^1$ represents methyl, ethyl, n-propyl, i-propyl, n-butyl, i-butyl, s-butyl, t-butyl, cyclopropyl or cyclobutyl; and A$^2$ represents methyl, ethyl, n-propyl, i-propyl, n-butyl, i-butyl, s-butyl, t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl, benzyl, methylbenzyl, chlorobenzyl, fluorobenzyl, or trifluoromethylbenzyl.

3. A compound according to claim 2, in which

Ar represents orthophenylene;

E represents a group of the formula:

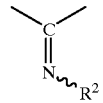

R$^2$ represents methoxy;
G represents —CH$_2$—Q— or —Q—CH$_2$—;
Q represents oxygen;

R represents furyl which is attached to E via a carbon atom and which is optionally substituted by methyl, methoxy or hydroxy; and Z represents phenyl, which is optionally substituted one to three times by substituents independently selected from the group consisting of:

a) fluorine, chlorine or bromine;
b) cyano;
c) methyl, ethyl, n-propyl, i-propyl, n-butyl, i-butyl, s-butyl, t-butyl, methoxy, ethoxy, n-propoxy, i-propoxy, methylthio, ethylthio, n-propylthio, i-propylthio, methylsulfinyl, ethylsulfinyl, methylsulfonyl or ethylsulfonyl;
d) trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulfinyl or trifluoromethylsulfonyl;
e) methoxycarbonyl or ethoxycarbony;
f) methylenedioxy or ethylenedioxy, each of which is attached to said phenyl twice, and is optionally mono- to tetrasubstituted independently by fluorine, chlorine, methyl, trifluoromethyl or ethyl; and
g) a grouping of the formula:

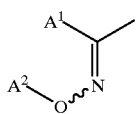

in which
A$^1$ represents methyl, ethyl, n-propyl, i-propyl, n-butyl, i-butyl, s-butyl, t-butyl, cyclopropyl or cyclobutyl; and
A$^2$ represents methyl, ethyl, n-propyl, i-propyl, n-butyl, i-butyl, s-butyl, t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl, benzyl, methylbenzyl, chlorobenzyl, fluorobenzyl, or trifluoromethylbenzyl.

4. A compound according to claim 2, in which
Ar represents orthophenylene;
E represents a group of the formula:

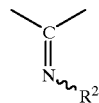

R$^2$ represents methoxy;
G represents —O—CH$_2$—;
R represents furyl which is attached to E via a carbon atom and which is optionally substituted by methyl, methoxy or hydroxy; and
Z represents phenyl, which is optionally substituted one to three times by substituents independently selected from the group consisting of:

a) fluorine, chlorine or bromine;
b) cyano;
c) methyl, ethyl, n-propyl, i-propyl, n-butyl, i-butyl, s-butyl, t-butyl, methoxy, ethoxy, n-propoxy, i-propoxy, methylthio, ethylthio, n-propylthio, i-propylthio, methylsulfinyl, ethylsulfinyl, methylsulfonyl or ethylsulfonyl;
d) trifluoromethyl, difluoromethoxy, trifluoromethoxy, difluorochloromethoxy, trifluoroethoxy, difluoromethylthio, difluorochloromethylthio, trifluoromethylthio, trifluoromethylsulfinyl or trifluoromethylsulfonyl;
e) methoxycarbonyl or ethoxycarbony;
f) methylenedioxy or ethylenedioxy, each of which is attached to said phenyl twice, and is optionally mono- to tetrasubstituted independently by fluorine, chlorine, methyl, trifluoromethyl or ethyl; and
g) a grouping of the formula:

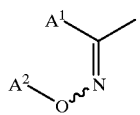

in which
A$^1$ represents methyl, ethyl, n-propyl, i-propyl, n-butyl, i-butyl, s-butyl, t-butyl, cyclopropyl or cyclobutyl; and
A$^2$ represents methyl, ethyl, n-propyl, i-propyl, n-butyl, i-butyl, s-butyl, t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl, benzyl, methylbenzyl, chlorobenzyl, fluorobenzyl, or trifluoromethylbenzyl.

5. A fungicidal composition comprising a fungicidally effective amount of a compound according to claim 1 and a carrier.

6. A method of combating fungi comprising applying to fungi or their habitat a fungicidally effective amount of a compound according to claim 1.

7. A fungicidal composition comprising a fungicidally effective amount of a compound according to claim 2 and a carrier.

8. A method of combating fungi comprising applying to fungi or their habitat a fungicidally effective amount of a compound according to claim 2.

* * * * *